United States Patent
Kudo et al.

(10) Patent No.: US 12,145,888 B2
(45) Date of Patent: Nov. 19, 2024

(54) ZIRCONIA MOLDED BODY AND PRE-SINTERED BODY CAPABLE OF BEING SINTERED IN SHORT TIME

(71) Applicant: KURARAY NORITAKE DENTAL INC., Kurashiki (JP)

(72) Inventors: Yasutaka Kudo, Aichi (JP); Yoshihisa Ito, Aichi (JP)

(73) Assignee: KURARAY NORITAKE DENTAL INC., Kurashiki (JP)

(*) Notice: Subject to any disclaimer, the term of this patent is extended or adjusted under 35 U.S.C. 154(b) by 473 days.

(21) Appl. No.: 17/436,417

(22) PCT Filed: Mar. 5, 2020

(86) PCT No.: PCT/JP2020/009491
§ 371 (c)(1),
(2) Date: Sep. 3, 2021

(87) PCT Pub. No.: WO2020/179877
PCT Pub. Date: Sep. 10, 2020

(65) Prior Publication Data
US 2022/0135486 A1     May 5, 2022

(30) Foreign Application Priority Data
Mar. 6, 2019 (JP) ................. 2019-040984

(51) Int. Cl.
| | | |
|---|---|---|
| C04B 35/488 | (2006.01) | |
| C04B 35/64 | (2006.01) | |
| C04B 35/645 | (2006.01) | |
| C09K 11/02 | (2006.01) | |
| C09K 11/77 | (2006.01) | |

(52) U.S. Cl.
CPC ............ *C04B 35/488* (2013.01); *C04B 35/64* (2013.01); *C04B 35/645* (2013.01); *C09K 11/02* (2013.01); *C09K 11/77* (2013.01); *C04B 2235/3225* (2013.01); *C04B 2235/3246* (2013.01); *C04B 2235/5445* (2013.01); *C04B 2235/5454* (2013.01); *C04B 2235/656* (2013.01); *C04B 2235/661* (2013.01); *C04B 2235/76* (2013.01); *C04B 2235/762* (2013.01); *C04B 2235/765* (2013.01); *C04B 2235/96* (2013.01); *C04B 2235/9653* (2013.01); *C04B 2235/9661* (2013.01)

(58) Field of Classification Search
CPC ....... C09K 11/02; C04B 35/488; C04B 35/64; C04B 2235/3246; C04B 2235/5445; C04B 2235/5454; C04B 2235/3225; C04B 2235/656; C04B 2235/661; C04B 2235/76; C04B 2235/765; C04B 2235/9653; C04B 2235/9661; C04B 2235/96

See application file for complete search history.

(56) References Cited

U.S. PATENT DOCUMENTS

| | | | |
|---|---|---|---|
| 11,401,461 B2 * | 8/2022 | Kudo | .......... A61K 6/76 |
| 2013/0172441 A1 | 7/2013 | Takahata et al. | |
| 2016/0310245 A1 | 10/2016 | Fujisaki et al. | |
| 2019/0231651 A1 * | 8/2019 | Ito | ............. A61C 5/70 |
| 2020/0317581 A1 | 10/2020 | Ito | |
| 2020/0369573 A1 * | 11/2020 | Kudo | ........... A61C 13/081 |
| 2021/0102115 A1 * | 4/2021 | Kudo | ............. C04B 35/63424 |

FOREIGN PATENT DOCUMENTS

| | | | |
|---|---|---|---|
| JP | 2000-159621 A | 6/2000 | |
| JP | 2002-145663 A | 5/2002 | |
| JP | 2008-21 4168 A | 9/2008 | |
| JP | 2014-34476 A | 2/2014 | |
| JP | 2015-143178 A | 8/2015 | |
| JP | 2016-117618 * | 6/2016 | |
| JP | 2016-117618 A | 6/2016 | |
| JP | 2019-26594 A | 2/2019 | |
| WO | WO 2012/042911 A1 | 4/2012 | |
| WO | WO 2014/126034 A1 | 8/2014 | |
| WO | WO 2018/056330 A1 | 3/2018 | |
| WO | WO 2018/056331 A1 | 3/2018 | |
| WO | WO-2019026809 A1 * | 2/2019 | ........... A61C 13/082 |
| WO | WO 2019026810 A1 * | 2/2019 | ........... A61C 13/081 |
| WO | WO-2019026811 A1 * | 2/2019 | ........... A61C 13/081 |

OTHER PUBLICATIONS

Translation for JP 2016-117618, Jun. 30, 2016.*
Extended European Search Report issued Oct. 27, 2022, in corresponding European Patent Application No. 20765621.6, 10 pages.
International Search Report issued on Apr. 21, 2020 in PCT/JP2020/009491 filed on Mar. 5, 2020, 2 pages.

* cited by examiner

*Primary Examiner* — C Melissa Koslow
(74) *Attorney, Agent, or Firm* — Oblon, McClelland, Maier & Neustadt, L.L.P.

(57) ABSTRACT

A zirconia sintered body may excel in translucency, strength, in linear light transmittance, and can be produced by short-time sintering without an HIP device, and be used in zirconia molded bodies and pre-sintered bodies from which such a zirconia sintered body can be obtained. A zirconia molded body with zirconia particles and 2.0 to 9.0 mol % yttria, having an average primary particle diameter less than 60 nm, and a monoclinic crystal system in a fraction of ≥55%. The zirconia molded body may have ≥1% undissolved yttria. A zirconia pre-sintered body may have such zirconia particles, wherein the zirconia pre-sintered body has ΔL*(W−B) of ≥5 through a thickness of 1.5 mm. A zirconia sintered body may have a fluorescent agent and 2.0 to 9.0 mol % yttria, and a crystal grain size of ≤180 nm.

18 Claims, No Drawings

ZIRCONIA MOLDED BODY AND PRE-SINTERED BODY CAPABLE OF BEING SINTERED IN SHORT TIME

CROSS-REFERENCE TO RELATED APPLICATIONS

The present application is the national stage of international application PCT/JP2020/009491, filed on Mar. 5, 2020, and claims the benefit of the filing date of Japanese Appl. No. 2019-040984, filed on Mar. 6, 2019.

TECHNICAL FIELD

The present invention relates to a zirconia molded body and pre-sintered body capable of being sintered in a short time, among others.

BACKGROUND ART

A zirconia sintered body containing yttria has been used for dental materials such as dental prostheses. Many of such dental prostheses are produced by forming a zirconia molded body of a desired shape, for example, a disc or prism shape, through the process of pressing zirconia particles or molding a slurry or a composition containing zirconia particles, followed by pre-sintering of the zirconia molded body into a pre-sintered body (mill blank), and subsequent sintering of the zirconia pre-sintered body after cutting (milling) it into the shape of the desired dental prosthesis.

In dental treatment, it is desired to complete zirconia sintering in a short time so as to achieve not only energy cost reduction but also treatment completion with no need for a patient to visit a dental clinic many times. Patent Literature 1 discloses a zirconia composition that can maintain translucency of a sintered body even with a reduced sintering time. However, the zirconia sintered body described in Patent Literature 1 has a large crystal grain size, and accordingly the translucency needs to be further improved. Reduction in crystal grain size of a zirconia sintered body is achieved by reduction in average primary particle diameter of zirconia particles before being sintered. However, Patent Literature 1 fails to disclose zirconia particles having a small average primary particle diameter.

Also, it has been confirmed that linear light transmittance improves by reducing and uniformizing the crystal grain size of a zirconia sintered body (see, for example, Patent Literature 2). To reduce and uniformize the crystal grain size of a zirconia sintered body, hot isostatic pressing (HIP) treatment is required. However, since an HIP device used for the HIP treatment is a special device classified as a high-pressure gas generator, it is difficult to say that a zirconia sintered body having high linear light transmittance can be obtained with ease.

CITATION LIST

Patent Literature

Patent Literature 1: WO 2018/056330
Patent Literature 2: JP 2008-214168 A

SUMMARY OF INVENTION

Technical Problem

It is an object of the present invention to provide a zirconia sintered body that excels in both translucency and strength and can be produced by short-time sintering. Another object of the present invention is to provide a zirconia molded body and a zirconia pre-sintered body from which such a zirconia sintered body can be obtained, and methods for conveniently producing these. In addition, the present invention also aims to provide a zirconia sintered body that exhibits excellent linear light transmittance with no use of an HIP device, a zirconia molded body and a zirconia pre-sintered body from which such a zirconia sintered body can be obtained, and methods for conveniently producing these.

Solution to Problem

The present inventors conducted intensive studies to achieve the foregoing objects, and found that a zirconia sintered body exhibits excellent translucency and strength can be obtained in a short time, by sintering a zirconia molded body under ordinary pressure, which comprises zirconia particles comprising 2.0 to 9.0 mol % yttria, has an average primary particle diameter of less than 60 nm, and comprises a monoclinic crystal system in a fraction of 55% or more, wherein the zirconia molded body comprises 1% or more undissolved yttria. It was also found that the novel zirconia sintered body is particularly preferred as, for example, dental materials such as dental prostheses, and is highly useful not only as a dental prosthesis used for the cervical region of a tooth but as a dental prosthesis used for the occlusal surface of a posterior tooth, and the incisal region of a front tooth. The present inventors completed the present invention after further studies based on these findings.

Specifically, the present invention relates to the following [1] to [22].

[1] A zirconia molded body comprising zirconia particles comprising 2.0 to 9.0 mol % yttria, having an average primary particle diameter of less than 60 nm, and comprising a monoclinic crystal system in a fraction of 55% or more, wherein the zirconia molded body comprises 1% or more undissolved yttria.

[2] The zirconia molded body according to [1], wherein the zirconia particles include 0.5 mass % or less zirconia particles having a particle diameter of more than 100 nm.

[3] The zirconia molded body according to [1] or [2], wherein the zirconia molded body has $\Delta L^*(W-B)$ of 5 or more through a thickness of 1.5 mm.

[4] The zirconia molded body according to any one of [1] to [3], wherein the zirconia molded body has a three-point flexural strength of 500 MPa or more after being sintered at 900 to 1,200° C. under ordinary pressure.

[5] The zirconia molded body according to any one of [1] to [4], wherein the zirconia molded body has a transmittance of 40% or more for light of 700 nm wavelength through a thickness of 0.5 mm after being sintered at 900 to 1,200° C. under ordinary pressure.

[6] The zirconia molded body according to any one of [1] to [5], wherein the zirconia molded body comprises a monoclinic crystal system in a fraction of 5% or less with respect to a tetragonal crystal system and a cubic crystal system after being sintered at 900 to 1,200° C. under ordinary pressure and then immersed in 180° C. hot water for 5 hours.

[7] The zirconia molded body according to any one of [1] to [6], wherein the zirconia molded body has $\Delta L^*(W-B)$ of 5 or more through a thickness of 1.5 mm after being sintered at 200 to 800° C.

[8] A zirconia pre-sintered body comprising: zirconia particles comprising 2.0 to 9.0 mol % yttria and comprising a monoclinic crystal system in a fraction of 55% or more; and 1% or more undissolved yttria, wherein the zirconia pre-sintered body has ΔL*(W−B) of 5 or more through a thickness of 1.5 mm.

[9] The zirconia pre-sintered body according to [8], wherein the zirconia pre-sintered body has a three-point flexural strength of 500 MPa or more after being sintered at 900 to 1,200° C. under ordinary pressure.

[10] The zirconia pre-sintered body according to [8] or [9], wherein the zirconia pre-sintered body has a transmittance of 40% or more for light of 700 nm wavelength through a thickness of 0.5 mm after being sintered at 900 to 1,200° C. under ordinary pressure.

[11] The zirconia pre-sintered body according to any one of [8] to [10], wherein the zirconia pre-sintered body comprises a monoclinic crystal system in a fraction of 5% or less with respect to a tetragonal crystal system and a cubic crystal system after being sintered at 900 to 1,200° C. under ordinary pressure and then immersed in 180° C. hot water for 5 hours.

[12] A method for producing a zirconia pre-sintered body, wherein the method uses the zirconia molded body of any one of [1] to [7].

[13] The method according to [12], comprising a step of pre-sintering the zirconia molded body of any one of [1] to [7] at 200 to 800° C.

[14] A zirconia sintered body comprising: a fluorescent agent; and 2.0 to 9.0 mol % yttria, wherein the zirconia sintered body has a crystal grain size of 180 nm or less.

[15] The zirconia sintered body according to [14], wherein the zirconia sintered body has a linear light transmittance of 1% or more through a thickness of 1.0 mm.

[16] The zirconia sintered body according to [14] or [15], wherein the zirconia sintered body has a three-point flexural strength of 500 MPa or more.

[17] The zirconia sintered body according to any one of [14] to [16], wherein the zirconia sintered body has a transmittance of 40% or more for light of 700 nm wavelength through a thickness of 0.5 mm.

[18] The zirconia sintered body according to any one of [14] to [17], wherein the zirconia sintered body comprises a monoclinic crystal system in a fraction of 5% or less with respect to a tetragonal crystal system and a cubic crystal system after being immersed in 180° C. hot water for 5 hours.

[19] A method for producing a zirconia sintered body, wherein the method uses the zirconia molded body of any one of [1] to [7].

[20] The method according to [19], comprising a step of sintering the zirconia molded body at 900 to 1,200° C. under ordinary pressure.

[21] A method for producing a zirconia sintered body, wherein the method uses the zirconia pre-sintered body of any one of [8] to [11].

[22] The method according to [21], comprising a step of sintering the zirconia pre-sintered body at 900 to 1,200° C. under ordinary pressure.

Advantageous Effects of Invention

According to the present invention, a zirconia sintered body is provided that excels in both translucency and strength and can be produced by short-time sintering. A zirconia molded body and a zirconia pre-sintered body are also provided from which such a zirconia sintered body can be obtained. The present invention also provides methods for conveniently producing these. In addition, according to a preferred embodiment of the present invention, a zirconia sintered body is provided that excels in linear light transmittance, with no use of an HIP device. A zirconia molded body and a zirconia pre-sintered body are also provided from which such a zirconia sintered body can be obtained. The present invention also provides methods for conveniently producing these.

DESCRIPTION OF EMBODIMENTS

The present invention includes a zirconia molded body comprising zirconia particles comprising 2.0 to 9.0 mol % yttria ($Y_2O_3$), having an average primary particle diameter of less than 60 nm, and comprising a monoclinic crystal system in a fraction of 55% or more, wherein the zirconia molded body comprises 1% or more undissolved yttria. With use of the zirconia molded body, it is possible to obtain a zirconia sintered body that excels in both translucency and strength and can be produced by short-time sintering. The present invention includes a zirconia pre-sintered body comprising: zirconia particles comprising 2.0 to 9.0 mol % yttria and comprising a monoclinic crystal system in a fraction of 55% or more; and 1% or more undissolved yttria, wherein the zirconia pre-sintered body has ΔL*(W−B) of 5 or more through a thickness of 1.5 mm. With use of the zirconia pre-sintered body, the zirconia sintered body can also be obtained. The following firstly describes a zirconia sintered body as an embodiment of the present invention. A zirconia sintered body of the present invention comprises: a fluorescent agent; and 2.0 to 9.0 mol % yttria, wherein the zirconia sintered body has a crystal grain size of 180 nm or less. It is to be noted that the following descriptions do not limit the present invention.

Zirconia Sintered Body

A zirconia sintered body of the present invention comprises a fluorescent agent. By containing a fluorescent agent, the zirconia sintered body exhibits fluorescence. The type of fluorescent agent is not particularly limited, and the fluorescent agent may be one or more fluorescent agents capable of emitting fluorescence under the light of any wavelength. Examples of such fluorescent agents include those containing metallic elements. Examples of the metallic elements include Ga, Bi, Ce, Nd, Sm, Eu, Gd, Tb, Dy, and Tm. The fluorescent agent may contain one of these metallic elements alone, or may contain two or more of these metallic elements. For advantages such as enhancing the effects of the present invention, the metallic elements are preferably Ga, Bi, Eu, Gd, and Tm, more preferably Bi and Eu. The fluorescent agent used to produce the zirconia sintered body of the present invention may be, for example, an oxide, hydroxide, acetate, or nitrate of the metallic elements above. The fluorescent agent may be, for example, $Y_2SiO_5$:Ce, $Y_2SiO_5$:Tb, (Y,Gd,Eu)$BO_3$, $Y_2O_3$:Eu, YAG:Ce, $ZnGa_2O_4$:Zn, or $BaMgAl_{10}O_{17}$:Eu.

The content of the fluorescent agent in the zirconia sintered body is not particularly limited, and may be appropriately adjusted according to such factors as the type of fluorescent agent, and the use of the zirconia sintered body. However, for advantages such as suitability as dental prostheses, the fluorescent agent content is preferably 0.001 mass % or more, more preferably 0.005 mass % or more, even more preferably 0.01 mass % or more, and is preferably 1 mass % or less, more preferably 0.5 mass % or less, even more preferably 0.1 mass % or less in terms of an oxide of the metallic element contained in the fluorescent agent, relative to the mass of the zirconia contained in the zirconia sintered body. With the fluorescent agent contained in an amount equal to or greater than these lower limits, the zirconia sintered body can produce fluorescence comparable to that of natural human teeth. With the fluorescent agent contained in an amount equal to or less than the foregoing upper limits, decrease of translucency and strength can be reduced.

The zirconia sintered body of the present invention may contain a colorant. By containing a colorant, the zirconia sintered body can have a color. The type of colorant is not particularly limited, and the colorant may be a known pigment commonly used to color ceramics, or a known dental liquid colorant. Examples of the colorant include colorants containing metallic elements, specifically, oxides, composite oxides, and salts containing metallic elements such as iron, vanadium, praseodymium, erbium, chromium, nickel, and manganese. The colorant may be a commercially available colorant, for example, such as the Prettau Colour Liquid manufactured by Zirkonzahn. The zirconia sintered body may contain one kind of colorant, or may contain two or more kinds of colorants.

The content of the colorant in the zirconia sintered body is not particularly limited, and may be appropriately adjusted according to such factors as the type of colorant, and the use of the zirconia sintered body. However, for advantages such as suitability as dental prostheses, the colorant content is preferably 0.001 mass % or more, more preferably 0.005 mass % or more, even more preferably 0.01 mass % or more, and is preferably 5 mass % or less, more preferably 1 mass % or less, even more preferably 0.5 mass % or less, and may be 0.1 mass % or less, or 0.05 mass % or less in terms of an oxide of the metallic element contained in the colorant, relative to the mass of the zirconia contained in the zirconia sintered body.

With the present invention, a zirconia sintered body having high linear light transmittance can be obtained. The zirconia sintered body of the present invention may contain a translucency adjuster for adjustment of translucency in the zirconia sintered body. Specific examples of the translucency adjuster include aluminum oxide, titanium oxide, silicon dioxide, zircon, lithium silicate, and lithium disilicate. The zirconia sintered body may contain one kind of translucency adjuster, or may contain two or more kinds of translucency adjusters.

The content of the translucency adjuster in the zirconia sintered body is not particularly limited, and may be appropriately adjusted according to such factors as the type of translucency adjuster, and the use of the zirconia sintered body. However, for advantages such as suitability as dental prostheses, the content of translucency adjuster is preferably 0.1 mass % or less relative to the mass of the zirconia contained in the zirconia sintered body.

The zirconia sintered body of the present invention contains 2.0 to 9.0 mol % yttria. The zirconia sintered body cannot have sufficient translucency with an yttria content of less than 2.0 mol %. The strength decreases when the yttria content in the zirconia sintered body is more than 9.0 mol %. For advantages such as producing a zirconia sintered body having improved translucency and strength, the yttria content in the zirconia sintered body is preferably 3.0 mol % or more, more preferably 4.0 mol % or more, and is preferably 8.0 mol % or less, more preferably 7.0 mol % or less. It is to be noted that the yttria content in the zirconia sintered body is a fraction (mol %) of the number of moles of yttria with respect to the total number of moles of zirconia and yttria.

It is important for the zirconia sintered body of the present invention to have a crystal grain size of 180 nm or less. Insufficient translucency is obtained with a crystal grain size of more than 180 nm. For advantages such as producing a zirconia sintered body having improved translucency, the crystal grain size is preferably 140 nm or less, more preferably 120 nm or less, even more preferably 110 nm or less, and may be 100 nm or less. The lower limit of crystal grain size is not particularly limited, and the crystal grain size may be, for example, 50 nm or more, or 70 nm or more. The crystal grain size of the zirconia sintered body can be determined by taking a micrograph of zirconia sintered body cross sections with a field emission scanning electron microscope (FE-SEM), and finding a mean value of diameters of circles corresponding to 10 arbitrarily selected particles from the micrograph (the diameters of true circles having the same areas as these particles).

The zirconia sintered body of the present invention excels in strength. The zirconia sintered body of the present invention has a three-point flexural strength of 500 MPa or more, preferably 600 MPa or more, more preferably 650 MPa or more, even more preferably 700 MPa or more, particularly preferably 800 MPa or more. With the three-point flexural strength falling in these ranges, the zirconia sintered body of the present invention can have a reduced chance of breaking or fracturing in the mouth when used as, for example, a dental prosthesis. The upper limit of three-point flexural strength is not particularly limited, and the three-point flexural strength may be, for example, 1,500 MPa or less, or 1,000 MPa or less. The three-point flexural strength of zirconia sintered body can be measured in compliance with ISO 6872:2015.

The zirconia sintered body of the present invention excels in translucency. The zirconia sintered body of the present invention has a transmittance of preferably 40% or more, more preferably 45% or more, and may have a transmittance of 46% or more, 48% or more, 50% or more, or 52% or more for light of 700 nm wavelength through a thickness of 0.5 mm. With the transmittance falling in these ranges, the zirconia sintered body can more easily satisfy the level of translucency required for the incisal region when used as, for example, a dental prosthesis. The upper limit of transmittance is not particularly limited, and the transmittance may be, for example, 60% or less, or 57% or less. The transmittance of zirconia sintered body for light of 700 nm wavelength through a thickness of 0.5 mm may be measured with a spectrophotometer. For example, the transmittance can be measured with an integrating sphere by measuring light from a light source passing and scattering on a specimen, using a spectrophotometer (Hitachi spectrophotometer, Model U-3900H manufactured by Hitachi High-Technologies Corporation). In the measurement, the transmittance for light of 700 nm wavelength may be determined after measuring transmittance in a wavelength region of 300 to 750 nm. The specimen used for measurement may be a disc-shaped zirconia sintered body having mirror polished surfaces and measuring 15 mm in diameter and 0.5 mm in thickness.

The zirconia sintered body of the present invention preferably excels in linear light transmittance. The zirconia sintered body of the present invention has a linear light transmittance of preferably 1% or more, more preferably 3% or more, or may be 5% or more, 7% or more, or 10% or more, through a thickness of 1.0 mm. With the linear light transmittance falling in these ranges, the zirconia sintered body can more easily satisfy the level of translucency required for the incisal region when used as, for example, a dental prosthesis. The upper limit of linear light transmittance is not particularly limited, and the linear light transmittance may be, for example, 60% or less, or 50% or less. The linear light transmittance of zirconia sintered body through a thickness of 1.0 mm may be measured with a turbidimeter. For example, the linear light transmittance can be measured with an integrating sphere by measuring light from a light source passing and scattering on a specimen, using a turbidimeter (Haze Meter NDH 4000 manufactured by Nippon Denshoku Industries Co., Ltd.). In the measurement, the linear light transmittance is measured preferably in compliance with ISO 13468-1:1996 and JIS K 7361-1:1997, and the haze is measured preferably in compliance with ISO 14782-1:1999 and JIS K 7136:2000. The specimen used for measurement may be a disc-shaped zirconia sintered body having mirror polished surfaces and measuring 15 mm in diameter and 1.0 mm in thickness.

The predominant crystal phase of the zirconia sintered body of the present invention may be a tetragonal crystal system or a cubic crystal system. However, a fraction of the cubic crystal system in the zirconia sintered body is preferably higher than that of the tetragonal crystal system. The zirconia sintered body of the present invention is preferably at least 30% cubic crystal system, more preferably at least 50% cubic crystal system. The fraction of the cubic crystal system in the zirconia sintered body may be determined by crystal phase analysis. Specifically, the fraction of the cubic crystal system may be determined by X-ray diffraction (XRD) analysis of a mirror finished surface portion of the zirconia sintered body, using the following formula.

$$f_c = 100 \times I_c/(I_m + I_t + I_c)$$

Here, $f_c$ represents the fraction (%) of the cubic crystal system in the zirconia sintered body, $I_m$ represents the height of a peak (a peak attributed to the (11-1) plane of a monoclinic crystal system) near 2θ=28 degrees, $I_t$ represents the height of a peak (a peak attributed to the (111) plane of a tetragonal crystal system) near 2θ=30 degrees, and represents the height of a peak (a peak attributed to the (111) plane of the cubic crystal system) near 2θ=30 degrees. When the peak near 2θ=30 degrees appears as a peak attributed to a mixed phase of the (111) plane of the tetragonal crystal system and the (111) plane of the cubic crystal system, and separation is difficult to achieve for the peak attributed to the (111) plane of the tetragonal crystal system and the peak attributed to the (111) plane of the cubic crystal system, $I_t$ and $I_c$ can be determined by determining the ratio of tetragonal crystal and cubic crystal system using a technique such as the Rietveld method, and then multiplying the ratio by the height ($I_{t+c}$) of the peak attributed to the mixed phase.

In the zirconia sintered body of the present invention, the fraction of monoclinic crystal system with respect to tetragonal crystal system and cubic crystal system after the zirconia sintered body is immersed in 180° C. hot water for 5 hours is preferably 5% or less, more preferably 3% or less, even more preferably 1% or less. With the fraction falling in these ranges, volume changes due to aging can be reduced, and breakage can be prevented when the zirconia sintered body is used as, for example, a dental prosthesis. The fraction can be determined by mirror polishing a surface of the zirconia sintered body, and measuring the mirror polished surface portion by X-ray diffraction (XRD) analysis after the zirconia sintered body is immersed in 180° C. hot water for 5 hours, using the following formula.

$$f_m = 100 \times I_m/(I_{t+c})$$

Here, $f_m$ represents the fraction (%) of the monoclinic crystal system with respect to the tetragonal crystal system and the cubic crystal system in the zirconia sintered body immersed in 180° C. hot water for 5 hours, $I_t$ represents the height of a peak (a peak attributed to the (11-1) plane of the monoclinic crystal) near 2θ=28 degrees, and $I_{t+c}$ represents the height of a peak (a peak attributed to a mixed phase of the (111) plane of the tetragonal crystal system and the (111) plane of the cubic crystal system) near 2θ=30 degrees. When $I_{t+c}$ cannot be easily specified as a result of the peak near 2θ=30 degrees separately appearing as a peak attributed to the (111) plane of the tetragonal crystal system and a peak attributed to the (111) plane of the cubic crystal system, $I_{t+c}$ can be determined as the sum of the height ($I_t$) of the peak attributed to the (111) plane of the tetragonal crystal system and the height ($I_c$) of the peak attributed to the (111) plane of the cubic crystal system.

The method of production of the zirconia sintered body of the present invention comprises using the zirconia molded body of the present invention described below, and preferably comprises a step of sintering the zirconia molded body at 900 to 1,200° C. under ordinary pressure. Alternatively, the method of production of the zirconia sintered body of the present invention may use the zirconia pre-sintered body of the present invention described below, and preferably includes a step of sintering the zirconia pre-sintered body at 900 to 1,200° C. under ordinary pressure. With these producing methods, it is possible to easily produce the zirconia sintered body of the present invention that excels in both translucency and strength and can be produced by short-time sintering.

Zirconia Molded Body

The zirconia molded body of the present invention comprises zirconia particles comprising 2.0 to 9.0 mol % yttria, having an average primary particle diameter of less than 60 nm, and comprising a monoclinic crystal system in a fraction of 55% or more, wherein the zirconia molded body comprises 1% or more undissolved yttria. With use of the zirconia molded body, it is possible to obtain a zirconia sintered body that excels in both translucency and strength and can be produced by short-time sintering.

When producing a zirconia sintered body containing a fluorescent agent, it is preferable that the fluorescent agent be contained in the zirconia molded body. The content of the fluorescent agent in the zirconia molded body of the present invention may be appropriately adjusted according to, for example, the content of the fluorescent agent in the zirconia sintered body to be produced. Specifically, the content of the fluorescent agent in the zirconia molded body is preferably 0.001 mass % or more, more preferably 0.005 mass % or more, even more preferably 0.01 mass % or more, and is preferably 1 mass % or less, more preferably 0.5 mass % or less, even more preferably 0.1 mass % or less in terms of an oxide of the metallic element contained in the fluorescent agent, relative to the mass of the zirconia contained in the zirconia molded body.

When producing a zirconia sintered body containing a colorant, it is preferable that the colorant be contained in the zirconia molded body. The content of the colorant in the zirconia molded body of the present invention may be appropriately adjusted according to, for example, the content of the colorant in the zirconia sintered body to be produced. Specifically, the content of the colorant in the zirconia molded body is preferably 0.001 mass % or more, more preferably 0.005 mass % or more, even more preferably 0.01 mass % or more, and is preferably 5 mass % or less, more preferably 1 mass % or less, even more preferably 0.5 mass % or less, and may be 0.1 mass % or less, or 0.05 mass % or less in terms of an oxide of the metallic element contained in the colorant, relative to the mass of the zirconia contained in the zirconia molded body.

When producing a zirconia sintered body containing a translucency adjuster, it is preferable that the translucency adjuster be contained in the zirconia molded body. The content of the translucency adjuster in the zirconia molded body of the present invention may be appropriately adjusted according to, for example, the content of the translucency adjuster in the zirconia sintered body to be produced. Specifically, the content of the translucency adjuster in the zirconia molded body is preferably 0.1 mass % or less relative to the mass of the zirconia contained in the zirconia molded body.

The yttria content in the zirconia molded body of the present invention may be the same as the yttria content in the zirconia sintered body to be produced, within a range of 2.0 to 9.0 mol %. Specifically, the yttria content in the zirconia molded body is 2.0 mol % or more, preferably 3.0 mol % or more, more preferably 4.0 mol % or more, and is 9.0 mol % or less, preferably 8.0 mol % or less, more preferably 7.0 mol % or less. It is to be noted that the yttria content in the zirconia molded body is a fraction (mol %) of the number of moles of yttria with respect to the total number of moles of zirconia and yttria.

The density of the zirconia molded body of the present invention is not particularly limited, and varies with factors such as the method of production of the zirconia molded body. However, for advantages such as producing a more compact zirconia sintered body, the density is preferably 3.0 g/cm$^3$ or more, more preferably 3.2 g/cm$^3$ or more, even more preferably 3.4 g/cm$^3$ or more. The upper limit of density is not particularly limited, and may be, for example, 6.0 g/cm$^3$ or less, or 5.8 g/cm$^3$ or less.

The shape of the zirconia molded body of the present invention is not particularly limited, and may be chosen as desired according to use. However, for example, considering ease of handing of when producing a zirconia pre-sintered body to be used as a mill blank for producing a dental material such as a dental prosthesis, the zirconia molded body preferably has a disc or a prism shape (e.g., rectangular). By using a technique such as stereolithography, a shape corresponding to the shape desired for the product zirconia sintered body can be imparted to the zirconia molded body during its production, as will be described later. The present invention also encompasses zirconia molded bodies having such desired shapes. The zirconia molded body may have a monolayer structure or a multilayer structure. With a multilayered zirconia molded body, the resulting zirconia sintered body can have a multilayer structure, which allows translucency and other physical properties to be locally altered.

The zirconia molded body of the present invention preferably has high translucency. It is possible to produce, from such a zirconia molded body, a zirconia sintered body having high linear light transmittance and a zirconia pre-sintered body from which a zirconia sintered body having high linear light transmittance can be produced. Specifically, the zirconia molded body of the present invention has $\Delta L^*(W-B)$ of preferably 5 or more, more preferably 8 or more, and may be 10 or more, through a thickness of 1.5 mm. Here, $\Delta L^*(W-B)$ indicates the difference between lightness on a white background (L*) and lightness on a black background (L*). Specifically, $\Delta L^*(W-B)$ indicates the difference between an L* value on the white background and an L* value on the black background (JIS Z 8781-4: 2013 colorimetry-Part 4: CIE 1976 L*, a*, b*, color space). The white background and the black background respectively indicate a white part and a black part on a hiding-chart specified in JIS K 5600-4-1: 1999, Part 4, Section 1. With the $\Delta L^*(W-B)$ in the range as above, a zirconia sintered body having high linear light transmittance can be obtained after being sintered under ordinary pressure. The upper limit of $\Delta L^*(W-B)$ is not particularly limited. For example, the $\Delta L^*(W-B)$ may be 30 or less, or from the viewpoint of esthetic quality, may be 25 or less. The $\Delta L^*(W-B)$ of zirconia molded body through a thickness of 1.5 mm may be measured with a spectrophotometer. For example, the $\Delta L^*(W-B)$ can be measured with a spectrophotometer (CM-3610A manufactured by Konica Minolta Japan, Inc., geometric condition c (di: 8°, de: 8°), diffuse illumination: 8° light reception, measurement mode SCI, measurement diameter/illumination diameter=φ8 mm/φ11 mm), and calculated with color management software SpectraMagic NX ver. 2.5 manufactured by Konica Minolta Co., Ltd. In the measurement, the $\Delta L^*(W-B)$ may be determined by using F11 as a light source. The specimen used for measurement may be a disc-shaped zirconia molded body measuring 20 mm in diameter and 1.5 mm in thickness.

For considerations such as ease of handling, the zirconia molded body of the present invention has a biaxial flexural strength in a range of preferably 2 to 10 MPa, more preferably 5 to 8 MPa. The biaxial flexural strength of zirconia molded body can be measured in compliance with JIS T 6526:2018.

The zirconia molded body of the present invention has a crystal grain size of preferably 180 nm or less after being sintered at 900 to 1,200° C. for 10 minutes under ordinary pressure (after being formed into a zirconia sintered body). In this way, the zirconia sintered body of the present invention having excellent translucency can be produced with ease. For advantages such as producing a zirconia sintered body having even higher translucency, the crystal grain size is more preferably 140 nm or less, even more preferably 120 nm or less, further even more preferably 110 nm or less, and may be 100 nm or less. The lower limit of crystal grain size is not particularly limited, and the crystal grain size may be, for example, 50 nm or more, or 70 nm or more. Here, the crystal grain size is a measured value obtained in the same manner as in the crystal grain size measurement described above in conjunction with the zirconia sintered body.

The zirconia molded body of the present invention has a three-point flexural strength of preferably 500 MPa or more after being sintered at 900 to 1,200° C. for 10 minutes under ordinary pressure (after being formed into a zirconia sintered body).

In this way, the zirconia sintered body of the present invention having excellent strength can be produced with ease. For advantages such as producing a zirconia sintered body having even higher strength, the three-point flexural strength is more preferably 600 MPa or more, even more preferably 650 MPa or more, further even more preferably 700 MPa or more, particularly preferably 800 MPa or more. The upper limit of three-point flexural strength is not particularly limited, and the three-point flexural strength may be, for example, 1,500 MPa or less, or 1,000 MPa or less. Here, the three-point flexural strength is a measured value obtained in the same manner as in the three-point flexural strength measurement described above in conjunction with the zirconia sintered body.

The zirconia molded body of the present invention has a transmittance of preferably 40% or more for light of 700 nm wavelength through a thickness of 0.5 mm after being sintered at 900 to 1,200° C. under ordinary pressure (after being formed into a zirconia sintered body). In this way, the zirconia sintered body of the present invention having excellent translucency can be produced with ease. For advantages such as producing a zirconia sintered body having even higher translucency, the transmittance is more preferably 45% or more, and may be 46% or more, 48% or more, 50% or more, or 52% or more. In addition, most preferably, the transmittance for light of 700 nm wavelength through a thickness of 0.5 mm after sintering for 10 minutes as the condition of the sintering time satisfies the above range. The upper limit of transmittance is not particularly limited, and the transmittance may be, for example, 60% or less, or 57% or less. Here, the transmittance is a measured value obtained in the same manner as in the measurement of transmittance for light of 700 nm wavelength through a thickness of 0.5 mm described above in conjunction with the zirconia sintered body.

The zirconia molded body of the present invention has a linear light transmittance of preferably 1% or more, more preferably 3% or more, even more preferably 5% or more, particularly preferably 7% or more, and may be 10% or more, through a thickness of 1.0 mm after being sintered at 900 to 1,200° C. for 10 minutes under ordinary pressure (after being formed into a zirconia sintered body). With the linear light transmittance falling in these ranges, the zirconia sintered body can more easily satisfy the level of translucency required for the incisal region when used as, for example, a dental prosthesis. The upper limit of linear light transmittance is not particularly limited, and the linear light transmittance may be, for example, 60% or less, or 50% or less. The linear light transmittance can be measured in the same manner as in the measurement of linear light transmittance through a thickness of 1.0 mm described above in conjunction with the zirconia sintered body.

Method of Production of Zirconia Molded Body

The method of production of the zirconia molded body of the present invention is not particularly limited as long as the effects of the present invention are exhibited. However, for easy production of the zirconia sintered body of the present invention that excels in both translucency and strength and can be produced by short-time sintering, the method of production of the zirconia molded body of the present invention is preferably a method that includes a molding step of molding zirconia particles.

The yttria content in the zirconia particles used is preferably the same as the yttria content in the zirconia molded body, and, in turn, the yttria content in the zirconia pre-sintered body and the zirconia sintered body to be produced. Specifically, the yttria content in the zirconia particles is preferably 2.0 mol % or more, more preferably 3.0 mol % or more, even more preferably 4.0 mol % or more, and is preferably 9.0 mol % or less, more preferably 8.0 mol % or less, even more preferably 7.0 mol % or less. It is to be noted that the yttria content in the zirconia particles is a fraction (mol %) of the number of moles of yttria with respect to the total number of moles of zirconia and yttria.

From the viewpoint of obtaining a zirconia sintered body that excels in both translucency and strength and can be produced by short-time sintering, it is important for the zirconia particles used to have an average primary particle diameter of less than 60 nm. Also, the zirconia molded body of the present invention preferably has a particle size distribution in which zirconia particles having a particle diameter of more than 100 nm are 0.5 mass % or less with respect to the total amount of the zirconia particles. In this way, the zirconia molded body of the present invention, and, in turn, the zirconia pre-sintered body and the zirconia sintered body of the present invention can be obtained with ease. For considerations such as ease of production of the zirconia molded body of the present invention, and, in turn, the zirconia pre-sintered body and the zirconia sintered body of the present invention, the average primary particle diameter of the zirconia particles included in the resulting zirconia molded body is preferably 50 nm or less, more preferably 30 nm or less, even more preferably 20 nm or less, and may be 10 nm or less, and is preferably 1 nm or more, more preferably 5 nm or more. For considerations such as ease of production of the zirconia molded body of the present invention, and, in turn, the zirconia pre-sintered body and the zirconia sintered body of the present invention, and ease of obtaining a desired linear light transmittance, zirconia particles having a particle diameter of more than 100 nm are preferably 0.3 mass % or less, more preferably 0.2 mass % or less, particularly preferably 0.1 mass % or less, and may be 0.05 mass % or less. The average primary particle diameter of zirconia particles can be determined by, for example, taking a micrograph of zirconia particles (primary particles) with a transmission electron microscope (TEM), and finding a mean value of particle diameters (maximum diameters) measured for arbitrarily chosen 100 particles from the photographed image. The content of the zirconia particles having a particle diameter of more than 100 nm may be measured with for example a zeta potential measurement device (for example, a real-time zeta potential/nanoparticle size measurement device (DelsaMax PRO under trade name manufactured by Beckman Coulter Co., Ltd.) or a zeta potential/particle size/molecular weight measurement system (ELSZ-2000ZS under trade name manufactured by Otsuka Electronics Co., Ltd.)). For example, both amounts of zirconia particles before and after particle classification are measured, and an amount of zirconia particles having a particle diameter differing between the measured values (mass %) by more than 100 nm corresponds to the content of zirconia particles having a particle diameter of more than 100 nm.

The predominant crystal system of the zirconia particles used for the zirconia molded body of the present invention is a monoclinic crystal system, and it is important that the zirconia molded body of the present invention should include the monoclinic crystal system in a fraction $f_m$ of 55% or more with respect to the total amount of the monoclinic crystal system, a tetragonal crystal system, and a cubic crystal system. For advantages such as ease of obtaining the desired zirconia sintered body, the fraction $f_m$ of the monoclinic crystal system in the zirconia molded body is preferably 60% or more, more preferably 70% or more, even more preferably 80% or more, particularly preferably 90% or more, most preferably 95% or more with respect to the total amount of the monoclinic crystal system, the tetragonal crystal system, and the cubic crystal system. The fraction $f_m$ of the monoclinic crystal system in the zirconia molded body may be determined by X-ray diffraction (XRD) analysis, using the following formula.

$$f_m = 100 \times I_m / (I_m + I_{t+c})$$

Here, $f_m$ represents the fraction (%) of the monoclinic crystal system with respect to the tetragonal crystal system and the cubic crystal system in the zirconia molded body, $I_m$ represents the height of a peak (a peak attributed to the (11-1) plane of the monoclinic crystal system) near 2θ=28 degrees, and $I_{t+c}$ represents the height of a peak (a peak attributed to a mixed phase of the (111) plane of the tetragonal crystal system and the (111) plane of the cubic crystal system) near 2θ=30 degrees. When $I_{t+c}$ cannot be easily specified as a result of the peak near 2θ=30 degrees separately appearing as a peak attributed to the (111) plane of the tetragonal crystal system and a peak attributed to the (111) plane of the cubic crystal system, $I_{t+c}$ can be determined as the sum of the height ($I_t$) of the peak attributed to the (111) plane of the tetragonal crystal system and the height ($I_c$) of the peak attributed to the (111) plane of the cubic crystal system.

In the zirconia molded body of the present invention, yttria is used as a stabilizer. At least a part of the zirconia crystals exists as a monoclinic crystal system by the presence of yttria, and at least a part of yttria is present in an undissolved form in zirconia as a solid solution. It can be confirmed that part of yttria is not dissolved in zirconia as a solid solution for example by an X-ray diffraction (XRD) pattern. The presence of a peak derived from yttria in an XRD pattern of a composition means that the composition contains yttria that is not dissolved in zirconia as a solid solution. A peak derived from yttria is basically not observable in an XRD pattern when yttria has fully dissolved as a solid solution. It is, however, possible, depending on the crystal state or other conditions of yttria, that yttria may not be dissolved in zirconia as a solid solution even when yttria does not produce a peak in the XRD pattern. Yttria can be thought of having dissolved in zirconia as a solid solution mostly, basically completely, when the predominant crystal system of zirconia is a tetragonal crystal system and/or a cubic crystal system and there is no peak attributed to yttria in the XRD pattern. It is to be noted that a stabilizer other than yttria may be used in combination in the present invention.

A stabilizer in the zirconia molded body of the present invention is yttria. In the zirconia molded body, the fraction $f_y$ of yttria that is not dissolved in zirconia as a solid solution (hereinafter, referred to as "undissolved yttria") is 1% or more, and for advantages such as ease of obtaining the desired zirconia sintered body, the fraction $f_y$ is preferably 2% or more, more preferably 3% or more. The upper limit of the fraction $f_y$ of undissolved yttria depends on the content of yttria in the zirconia molded body. The fraction $f_y$ may be 15% or less for an yttria content of 7.5 mol % or less with respect to the total mol of zirconia and yttria. For example, the fraction $f_y$ may be 7% or less for an yttria content of 3.5 mol % to 4.5 mol %. The fraction $f_y$ may be 10% or less for an yttria content of 5 mol % to 6 mol %. The fraction $f_y$ may be 11% or less for an yttria content of 5.5 mol % to 6.5 mol %. The fraction $f_y$ of undissolved yttria can be determined using the following formula.

$$f_y = 100 \times I_y / (I_y + I_m + I_{t+c})$$

Here, $f_y$ represents the fraction (%) of undissolved yttria with respect to zirconia in the zirconia molded body, $I_y$ represents the height of a peak (a peak attributed to the (111) plane of yttria) near 2θ=29 degrees, $I_m$ represents the height of a peak (a peak attributed to the (11-1) plane of the monoclinic crystal system) near 2θ=28 degrees, and $I_{t+c}$ represents the height of a peak (a peak attributed to a mixed phase of the (111) plane of the tetragonal crystal system and the (111) plane of the cubic crystal system) near 2θ=30 degrees. When $I_{t+c}$ cannot be easily specified as a result of the peak near 2θ=30 degrees separately appearing as a peak attributed to the (111) plane of the tetragonal crystal system and a peak attributed to the (111) plane of the cubic crystal system, $I_{t+c}$ can be determined as the sum of the height ($I_t$) of the peak attributed to the (111) plane of the tetragonal crystal system and the height ($I_t$) of the peak attributed to the (111) plane of the cubic crystal system. Also, when a stabilizer other than yttria is used in combination, the above formula is applicable to calculation of the percentage presence of undissolved stabilizer other than yttria by substituting a peak of the other stabilizer for $I_y$.

The method of preparation of zirconia particles is not particularly limited, and the zirconia particles may be prepared by using, for example, a breakdown process that pulverizes coarse particles into a fine powder, or a building-up process that synthesizes particles through nucleation and nuclear growth from atoms and ions. The building-up process is more preferred for obtaining high-purity, fine zirconia p articles.

The breakdown process may use, for example, a ball mill or bead mill for pulverization. Here, it is preferable to use microsize pulverization media, for example, pulverization media of 100 μm or less. Also, from the viewpoint of obtaining a desired linear light transmittance, it is preferable to classify the zirconia particles obtained after pulverization of coarse particles. Classification may be performed with known methods and devices, such as porous membranes (membrane filters having a pore diameter of 100 nm) and classifiers (wet classifier and dry classifier).

The building-up process may be, for example, vapor-phase pyrolysis, which is a process by which an oxoacid salt of high-vapor-pressure metal ions, or a high-vapor-pressure organometallic compound is decomposed under heat through vaporization to precipitate an oxide; vapor-phase reaction, which synthesizes particles through vapor-phase chemical reaction of a high-vapor-pressure metallic compound gas with a reactive gas; evaporative concentration, in which a feedstock material is heated to evaporate, and cooled rapidly in an inert gas of a predetermined pressure to condense the steam into a fine particle form; a melt process that forms a powder by cooling and solidifying small liquid droplets of melt; solvent evaporation, which causes precipitation in a supersaturated state created by increasing the concentration by evaporating the solvent in a solution; or a precipitation process in which the solute concentration is brought to a supersaturated state through reaction with a precipitating agent or hydrolysis, and a poorly soluble compound such as an oxide and hydroxide is precipitated through nucleation and nuclear growth.

The precipitation process can be sub-divided into processes that include: homogenous precipitation in which a precipitating agent is generated in a solution by chemical reaction to eliminate local heterogeneity in the concentration of precipitating agent; coprecipitation in which a plurality of metal ions coexisting in a solution is simultaneously precipitated by addition of a precipitating agent; a hydrolysis process that produces an oxide or hydroxide through hydrolysis from a metal salt solution, an alcohol solution of metal alkoxide or the like; and solvothermal synthesis that produces an oxide or hydroxide from a high-temperature high-pressure fluid. The solvothermal synthesis is further divided into processes that include hydrothermal synthesis that uses water as solvent, and supercritical synthesis that uses a supercritical fluid such as water or carbon dioxide as solvent.

Regardless of the building-up process, it is preferable to increase the precipitation rate to obtain finer zirconia particles. Also, from the viewpoint of obtaining a desired linear light transmittance, it is preferable to classify the zirconia particles obtained. Classification may be performed with known methods and devices, such as porous membranes (membrane filters having a pore diameter of 100 nm) and classifiers (wet classifier and dry classifier).

The zirconium source in the building-up process may be, for example, nitrate, acetate, chloride, or alkoxide. Specifically, for example, zirconium oxychloride, zirconium acetate, and zirconyl nitrate may be used.

The yttrium source may be, for example, nitrate, acetate, chloride, or alkoxide. Specifically, for example, yttrium chloride, yttrium acetate, and yttrium nitrate may be used.

As required, the zirconia particles may be subjected to a surface treatment in advance with a known surface treatment agent selected from, for example, organic compounds having acidic groups; fatty acid amides such as saturated fatty acid amides, unsaturated fatty acid amides, saturated fatty acid bisamides, and unsaturated fatty acid bisamides; and organometallic compounds such as silane coupling agents (organosilicon compounds), organic titanium compounds, organic zirconium compounds, and organic aluminum compounds. A surface treatment of zirconia particles allows for adjustments of miscibility with a liquid having a surface tension at 25° C. of 50 mN/m or less when such a liquid is contained in the dispersion medium of a slurry used when preparing a zirconia particle- and fluorescent agent-containing powder, as will be described later. A surface treatment also allows the zirconia particles to have adjusted miscibility with a polymerizable monomer, for example, when producing the zirconia molded body using a method that includes polymerizing a composition containing zirconia particles, a fluorescent agent, and a polymerizable monomer, as will be described later. The surface treatment agent is preferably an organic compound having an acidic group because of advantages such as desirable miscibility with a liquid having a surface tension at 25° C. of 50 mN/m or less, and the ability to increase the strength of the resulting zirconia molded body by improving the chemical bonding between the zirconia particles and a polymerizable monomer.

Examples of the organic compounds having acidic groups include organic compounds having at least one acidic group, such as a phosphoric acid group, a carboxylic acid group, a pyrophosphoric acid group, a thiophosphoric acid group, a phosphonic acid group, and a sulfonic acid group. Preferred are phosphoric acid group-containing organic compounds having at least one phosphoric acid group, and carboxylic acid group-containing organic compounds having at least one carboxylic acid group, of which the phosphoric acid group-containing organic compounds are more preferred. The zirconia particles may be subjected to a surface treatment with one type of surface treatment agent, or with two or more types of surface treatment agents. In the case where the zirconia particles are subjected to a surface treatment with two or more types of surface treatment agents, the surface treatment layer produced may be a surface treatment layer of a mixture of two or more surface treatment agents, or a surface treatment layer of a multilayer structure of a plurality of surface treatment layers.

Examples of the phosphoric acid group-containing organic compounds include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts thereof.

Examples of the carboxylic acid group-containing organic compounds include succinic acid, oxalic acid, octanoic acid, decanoic acid, stearic acid, polyacrylic acid, 4-methyloctanoic acid, neodecanoic acid, pivalic acid, 2,2-dimethylbutyric acid, 3,3-dimethylbutyric acid, 2,2-dimethylvaleric acid, 2,2-diethylbutyric acid, 3,3-diethylbutyric acid, naphthenic acid, cyclohexane dicarboxylic acid, (meth)acrylic acid, N-(meth)acryloylglycine, N-(meth)acryloylaspartic acid, O-(meth)acryloyltyrosine, N-(meth)acryloyltyrosine, N-(meth)acryloyl-p-aminobenzoic acid, N-(meth)acryloyl-o-aminobenzoic acid, p-vinyl benzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen maleate, 2-(2-(2-methoxyethoxy)ethoxy)acetic acid (commonly known as "MEEAA"), 2-(2-methoxyethoxy)acetic acid (commonly known as "MEAA"), succinic acid mono[2-(2-methoxyethoxy)ethyl]ester, maleic acid mono[2-(2-methoxyethoxy)ethyl]ester, glutaric acid mono[2-(2-methoxyethoxy)ethyl]ester, malonic acid, glutaric acid, 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propylsuccinate, and acid anhydrides, acid halides, alkali metal salts, and ammonium salts thereof.

It is also possible to use organic compounds having at least one acidic group different from the acidic groups mentioned above (e.g., a pyrophosphoric acid group, a thiophosphoric acid group, a phosphonic acid group, and a sulfonic acid group). For example, the organic compounds mentioned in WO2012/042911 may be used as such organic compounds.

Examples of the saturated fatty acid amides include palmitamide, stearamide, and behenamide. Examples of the unsaturated fatty acid amides include oleamide and erucamide. Examples of the saturated fatty acid bisamides include ethylene-bis-palmitamide, ethylene-bis-stearamide, and hexamethylene-bis-stearamide. Examples of the unsaturated fatty acid bisamides include ethylene-bis-oleamide, hexamethylene-bis-oleamide, and N,N'-dioleyl sebacamide.

Examples of the silane coupling agents (organosilicon compounds) include compounds represented by $R^1{}_nSiX_{4-n}$ (wherein $R^1$ is a substituted or unsubstituted hydrocarbon group of 1 to 12 carbon atoms, X is an alkoxy group of 1 to 4 carbon atoms, a hydroxyl group, a halogen atom, or a hydrogen atom, and n is an integer of 0 to 3, and $R^1$ and X each may be the same or different when a plurality of $R^1$ and X exists).

Specific examples of the silane coupling agents (organosilicon compounds) include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl-3,3,3-trifluoropropyldimethoxysilane, β-(3,4-epoxycyclohexyl) ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-(β-aminoethyl) γ-aminopropylmethyldimethoxysilane, N-(β-aminoethyl) γ-aminopropyltrimethoxysilane, N-(β-aminoethyl) γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane [3 to 12 carbon atoms between the (meth)acryloyloxy group and the silicon atom, for example, such as in γ-methacryloyloxypropyltrimethoxysilane], and ω(meth)acryloyloxyalkyltriethoxysilane [3 to 12 carbon atoms between the (meth)acryloyloxy group and the silicon atom, for example, such as in γ-methacryloyloxypropyltriethoxysilane]. As used herein, the notation "(meth)acryloyl" is meant to be inclusive of both methacryloyl and acryloyl.

Among these examples, silane coupling agents having functional groups are preferred. Particularly preferred are ω-(meth)acryloyloxyalkyltrimethoxysilane [3 to 12 carbon atoms between the (meth)acryloyloxy group and the silicon atom], ω-(meth)acryloyloxyalkyltriethoxysilane [3 to 12 carbon atoms between the (meth)acryloyloxy group and the silicon atom], vinyltrimethoxysilane, vinyltriethoxysilane, vinyltriacetoxysilane, and γ-glycidoxypropyltrimethoxysilane.

Examples of the organic titanium compounds include tetramethyl titanate, tetraisopropyl titanate, tetra-n-butyl titanate, butyl titanate dimers, and tetra(2-ethylhexyl)titanate.

Examples of the organic zirconium compounds include zirconium isopropoxide, zirconium n-butoxide, zirconium acetylacetonate, zirconyl acetate.

Examples of the organic aluminum compounds include aluminum acetylacetonate, and aluminum organic acid salt chelate compounds.

The surface treatment method is not particularly limited, and may be a known method, for example, such as a method the adds the surface treatment agent by spraying it while vigorously stirring the zirconia particles, or a method that disperses or dissolves the zirconia particles and the surface treatment agent in a suitable solvent, and removes the solvent. The solvent may be a dispersion medium containing a liquid having a surface tension at 25° C. of 50 mN/m or less, as will be described later. The zirconia particles and the surface treatment agent may be subjected to a reflux or a high-temperature high-pressure process (e.g., autoclaving) after being dispersed or dissolved.

According to the present invention, in producing a zirconia molded body using the method having a molding step of molding zirconia particles, the molding step is not particularly limited. However, for advantages such as ease of production of the zirconia molded body of the present invention, and, in turn, the zirconia pre-sintered body and the zirconia sintered body of the present invention, the molding step is preferably any one of the following steps:

(i) a step of slip casting a slurry containing zirconia particles;

(ii) a step of gel casting a slurry containing zirconia particles;

(iii) a step of pressing a powder containing zirconia particles;

(iv) a step of molding a composition containing zirconia particles and a resin; and (v) a step of polymerizing a composition containing zirconia particles and a polymerizable monomer.

Zirconia Particle-Containing Slurry

A method for preparing a zirconia particle-containing slurry is not particularly limited. For example, the zirconia particle-containing slurry may be one obtained after the breakdown or building-up process described above, or may be a commercially available product.

When producing a zirconia molded body containing a colorant and/or a translucency adjuster, and, in turn, a zirconia pre-sintered body and a zirconia sintered body containing a colorant and/or a translucency adjuster, the colorant and/or translucency adjuster may be added to the slurry containing zirconia particles and a fluorescent agent. In this case, it is preferable that the colorant and/or translucency adjuster be mixed into the zirconia particle-containing slurry in a liquid form such as a solution or a dispersion.

Zirconia Particle-Containing Powder

The method of preparation of a zirconia particle-containing powder is not particularly limited. However, for advantages such as obtaining a more homogenous zirconia sintered body of improved physical properties, it is preferable that the zirconia particle-containing powder be obtained by drying the zirconia particle-containing slurry. The slurry subjected to drying may additionally contain a fluorescent agent and/or a colorant and/or a translucency adjuster.

The drying method is not particularly limited, and may be, for example, spray drying, supercritical drying, freeze drying, hot-air drying, and drying under reduced pressure. For advantages such as inhibiting particle aggregation during the drying process and obtaining a more compact zirconia sintered body, it is preferable to use any of spray drying, supercritical drying, and freeze drying, more preferably spray drying or supercritical drying, even more preferably spray drying.

The zirconia particle-containing slurry to be dried may be a slurry containing water as dispersion medium. However, for advantages such as inhibiting particle aggregation during the drying process and obtaining a more compact zirconia sintered body, the slurry is preferably a slurry containing a dispersion medium other than water, for example, such as an organic solvent.

Examples of the organic solvent include alcohols such as methanol, ethanol, 1-propanol, 2-propanol, 1-butanol, 2-butanol, 2-methyl-2-propanol, 2-methoxyethanol, 2-ethoxyethanol, 2-(2-ethoxyethoxy)ethanol, diethylene glycol monobutyl ether, and glycerin; ketones such as acetone, and methyl ethyl ketone; ethers such as tetrahydrofuran, diethyl ether, diisopropyl ether, and 1,4-dioxane, and dimethoxyethane (including modified ethers such as propylene glycol monomethyl ether acetate (commonly known as "PGMEA"), preferably ether-modified ethers and/or ester-modified ethers, more preferably ether-modified alkylene glycols and/or ester-modified alkylene glycols); esters such as ethyl acetate and butyl acetate; hydrocarbons such as hexane and toluene; and halogenated hydrocarbons such as chloroform and carbon tetrachloride. These organic solvents may be used alone, or two or more thereof may be used in combination. Considering safety against the body and ease of removal, the organic solvent is preferably a water-soluble organic solvent. Specifically, the organic solvent is more preferably ethanol, 2-propanol, 2-methyl-2-propanol, 2-ethoxyethanol, 2-(2-ethoxyethoxy)ethanol, propylene glycol monomethyl ether acetate, acetone, or tetrahydrofuran.

When using spray drying in particular, it is preferable that the dispersion medium in the zirconia particle- and fluorescent agent-containing slurry to be dried contain a liquid having a surface tension at 25° C. of 50 mN/m or less because it enables a more compact zirconia sintered body to be obtained by inhibiting particle aggregation during the drying process. From this viewpoint, the surface tension of the liquid is preferably 40 mN/m or less, more preferably 30 mN/m or less.

The surface tension at 25° C. may be a value from, for example, the Handbook of Chemistry and Physics. For liquids that are not included in this reference, the values recited in WO2014/126034 are usable. The surface tensions at 25° C. of liquids that are not included in either of these documents may be determined by using a known measurement method, for example, such as the ring method or the Wilhelmy method. Preferably, the surface tension at 25° C. is measured using the automatic surface tensiometer CBVP-Z manufactured by Kyowa Interface Science Co., Ltd., or the SIGMA702 manufactured by KSV Instruments Ltd.

The liquid may be an organic solvent having the foregoing ranges of surface tension. The organic solvent may be any of the organic solvents exemplified above and having the foregoing ranges of surface tension. However, for advantages such as inhibiting particle aggregation during the drying process and obtaining a more compact zirconia sintered body, the organic solvent is preferably at least one selected from the group consisting of methanol, ethanol, 2-methoxyethanol, 1,4-dioxane, 2-ethoxyethanol, and 2-(2-ethoxyethoxy)ethanol, more preferably at least one selected from the group consisting of methanol, ethanol, 2-ethoxyethanol, and 2-(2-ethoxyethoxy)ethanol.

For advantages such as inhibiting particle aggregation during the drying process and obtaining a more compact zirconia sintered body, the content of the liquid in the dispersion medium is preferably 50 mass % or more, more preferably 80 mass % or more, even more preferably 95 mass % or more, particularly preferably 99 mass % or more.

A slurry containing a dispersion medium other than water can be obtained by replacing the dispersion medium in a slurry containing water as dispersion medium. The method used to replace the dispersion medium is not particularly limited. For example, a method may be used that removes water after adding a dispersion medium other than water (e.g., an organic solvent) to a slurry containing water as dispersion medium. In removing water, part or all of the dispersion medium other than water may be removed with water. The process of adding a dispersion medium other than water and the subsequent removal of water may be repeated multiple times. Alternatively, a method may be used that precipitates the dispersoid after adding a dispersion medium other than water to a slurry containing water as dispersion medium. It is also possible to replace the dispersion medium with a specific organic solvent in a slurry containing water as dispersion medium, followed by further replacement with another organic solvent.

The fluorescent agent may be added after the replacement of dispersion medium. However, for advantages such as obtaining a more homogenous zirconia sintered body of improved physical properties, the fluorescent agent is added preferably before the replacement of dispersion medium. Similarly, for advantages such as obtaining a more homogenous zirconia sintered body of improved physical properties, it is preferable to add a colorant and/or a translucency adjuster before the replacement of dispersion medium when adding a colorant and/or a translucency adjuster to the slurry, though these may be added after the dispersion medium is replaced.

The zirconia particle-containing slurry to be dried may be subjected to a dispersion process that involves heat and pressure, for example, such as a reflux process or a hydrothermal treatment. The zirconia particle-containing slurry to be subjected to the drying step may be subjected to a mechanical dispersion process using, for example, a roller mill, a colloid mill, a high-pressure spray disperser, an ultrasonic disperser, a vibration mill, a planetary mill, or a bead mill. The slurry may be subjected to only one of these processes, or two or more of these processes. The temperature of hydrothermal treatment is not particularly limited, and is preferably a temperature at which phase transformation of zirconia particles does not occur from the monoclinic crystal system to the tetragonal crystal system, for example, 180 to 300° C., 190 to 290° C., or 200 to 280° C. The time of hydrothermal treatment is not particularly limited. However, for advantages such as ease of controlling the fraction of undissolved yttria in the zirconia molded body and the zirconia pre-sintered body to fall within a desired range, and obtaining the desired zirconia sintered body, the time of hydrothermal treatment may be 5 minutes to 5 hours, 10 minutes to 4 hours, or 20 minutes to 3 hours. To obtain the desired zirconia molded body, zirconia pre-sintered body, and zirconia sintered body, for example when a slurry to be subjected to hydrothermal treatment includes both the zirconium source and the yttrium source, the time of hydrothermal treatment may be 5 minutes to 2 hours.

The zirconia particle-containing slurry to be dried may additionally contain one or more other components, for example, such as a binder, a plasticizer, a dispersant, an emulsifier, an antifoaming agent, a pH adjuster, and a lubricant. By containing such other components (particularly, for example, a binder, a dispersant, and an antifoaming agent), it may be possible to inhibit particle aggregation during the drying process, and obtain a more compact zirconia sintered body.

Examples of the binder include polyvinyl alcohol, methylcellulose, carboxymethylcellulose, acrylic binders, wax binders, polyvinyl butyral, polymethylmethacrylate, and ethylcellulose.

Examples of the plasticizer include polyethylene glycol, glycerin, propylene glycol, and dibutyl phthalic acid.

Examples of the dispersant include ammonium polycarboxylates (e.g., triammonium citrate), ammonium polyacrylates, acryl copolymer resins, acrylic acid ester copolymers, polyacrylic acids, bentonite, carboxymethylcellulose, anionic surfactants (for example, polyoxyethylene alkyl ether phosphate esters such as polyoxyethylene lauryl ether phosphate ester), non-ionic surfactants, oleic glycerides, amine salt surfactants, and oligosugar alcohols.

Examples of the emulsifier include alkyl ethers, phenyl ether, sorbitan derivatives, and ammonium salts.

Examples of the antifoaming agent include alcohols, polyethers, polyethylene glycol, silicone, and waxes.

Examples of the pH adjuster include ammonia, ammonium salts (including ammonium hydroxides such as tetramethylammonium hydroxide), alkali metal salts, and alkali-earth metal salts.

Examples of the lubricant include polyoxyethylene alkylate ether, and waxes.

For advantages such as inhibiting particle aggregation during the drying process and obtaining a more compact zirconia sintered body, the moisture content in the zirconia particle-containing slurry to be dried is preferably 3 mass % or less, more preferably 1 mass % or less, even more preferably 0.1 mass % or less. The moisture content may be measured with a Karl Fisher moisture content meter.

The drying conditions in the foregoing drying methods are not particularly limited, and may be appropriately selected from known drying conditions. When using an organic solvent as dispersion medium, it is preferable that drying be carried out in the presence of a nonflammable gas, more preferably in the presence of nitrogen, in order to reduce the risk of explosion during the drying process.

In the case of supercritical drying, the supercritical fluid is not particularly limited, and may be, for example, water or carbon dioxide. However, for advantages such as inhibiting particle aggregation and obtaining a more compact zirconia sintered body, the supercritical fluid is preferably carbon dioxide.

Composition Containing Zirconia Particles and Resin

The method of preparation of a composition containing zirconia particles and a resin is not particularly limited, and the composition may be obtained by, for example, mixing the zirconia particle-containing powder with a resin.

Composition Containing Zirconia Particles and Polymerizable Monomer

The method of preparation of a composition containing zirconia particles and a polymerizable monomer is not particularly limited, and the composition may be obtained by, for example, mixing the zirconia particle-containing powder with a polymerizable monomer.

(i) Slip Casting

In producing a zirconia molded body by the method that includes a step of slip casting a zirconia particle-containing slurry, the slip casting method is not particularly limited, and may be, for example, a method in which a zirconia particle-containing slurry is dried after being poured into a mold.

For advantages such as ease of pouring into a mold, and increasing the usable lifetime of a mold by preventing long drying times, the content of the dispersion medium in the zirconia particle-containing slurry used is preferably 80 mass % or less, more preferably 50 mass % or less, even more preferably 20 mass % or less.

The slurry may be poured into a mold under ordinary pressure. However, it is preferable for production efficiency that the slurry be poured into a mold under increased pressure conditions. The type of the mold used for slip casting is not particularly limited, and the mold may be, for example, a porous mold made of plaster, resin, ceramic, or the like. Resin molds and ceramic molds are desirable in terms of durability.

The zirconia particle-containing slurry used for slip casting may additionally contain one or more other components such as above, for example, such as a binder, a plasticizer, a dispersant, an emulsifier, an antifoaming agent, a pH adjuster, and a lubricant.

(ii) Gel Casting

In producing a zirconia molded body by the method that includes a step of gel casting a zirconia particle-containing slurry, the gel casting method is not particularly limited, and may be, for example, a method in which a zirconia particle and fluorescent agent-containing slurry is shaped into a wet body by a process such as gelation, followed by drying.

For advantages such as preventing long drying times and inhibiting cracking during drying, the content of the dispersion medium in the zirconia particle-containing slurry used is preferably 80 mass % or less, more preferably 50 mass % or less, even more preferably 20 mass % or less.

The gelation may be initiated by addition of, for example, a gelatinizer, or may be achieved by adding and polymerizing a polymerizable monomer. The type of the mold used is not particularly limited, and the mold may be, for example, a porous mold made of plaster, resin, ceramic, or the like, or a nonporous mold made of metal, resin, or the like.

The type of gelatinizer is not particularly limited, and, for example, a water-soluble gelatinizer may be used. Specifically, for example, agarose or gelatin may preferably be used. The gelatinizer may be one kind of gelatinizer used alone, or may be two or more kinds of gelatinizers used in combination. For considerations such as inhibiting cracking during sintering, the gelatinizer content is preferably 10 mass % or less, more preferably 5 mass % or less, even more preferably 1 mass % or less relative to the mass of the slurry after the gelatinizer is added.

The type of polymerizable monomer is not particularly limited. Examples of the polymerizable monomer include 2-hydroxyethyl(meth)acrylate, 3-hydroxypropyl(meth)acrylate, 4-hydroxybutyl(meth)acrylate, 6-hydroxyhexyl(meth)acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, and N,N-bis(2-hydroxyethyl)(meth)acrylamide. The polymerizable monomer may be used alone, or two or more thereof may be used in combination.

For considerations such as inhibiting cracking during sintering, the content of the polymerizable monomer is preferably 10 mass % or less, more preferably 5 mass % or less, even more preferably 1 mass % or less relative to the mass of the slurry after the polymerizable monomer is added.

When gelation is achieved by polymerization of the polymerizable monomer, the polymerization is carried out preferably with use of a polymerization initiator. The type of polymerization initiator is not particularly limited. However, the polymerization initiator is particularly preferably a photopolymerization initiator. The photopolymerization initiator may be appropriately selected from photopolymerization initiators commonly used in industry, preferably from photopolymerization initiators used in dentistry.

Specific examples of the photopolymerization initiator include (bis)acylphosphine oxides (including salts), thioxanthones (including salts such as quaternary ammonium salts), ketals, α-diketones, coumarins, anthraquinones, benzoinalkyl ether compounds, and α-aminoketone compounds. The photopolymerization initiator may be used alone, or two or more thereof may be used in combination. Among these, the photopolymerization initiator is preferably at least one selected from the group consisting of (bis)acylphosphine oxides and α-diketones. In this way, polymerization (gelation) can be achieved both in the ultraviolet region (including the near-ultraviolet region) and in the visible light region. Specifically, polymerization (gelation) can sufficiently proceed regardless of whether the light source is a laser such as an Ar laser or a He—Cd laser; or a light such as a halogen lamp, a xenon lamp, a metal halide lamp, a light emitting diode (LED), a mercury lamp, and a fluorescent lamp.

Examples of the acylphosphine oxides in the (bis)acylphosphine oxides include 2,4,6-trimethylbenzoyldiphenylphosphine oxide (commonly known as "TPO"), 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide.

Examples of the bisacylphosphine oxides in the (bis)acylphosphine oxides include bis(2,6-dichlorobenzoyl)phenylphosphine oxide, bis(2,6-dichlorobenzoyl)-2,5-dimethylphenylphosphine oxide, bis(2,6-dlichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,3,6-trimethylbenzoyl)-2,4,4-trimethylpentylphosphine oxide. It is also possible to use other compounds, including, for example, the compounds mentioned in JP-A-2000-159621.

Preferred among these (bis)acylphosphine oxides are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Preferred is camphorquinone, particularly when using a light source of the visible light region.

The zirconia particle-containing slurry used for gel casting may additionally contain one or more other components such as, for example, such as a binder, a plasticizer, a dispersant, an emulsifier, an antifoaming agent, a pH adjuster, and a lubricant, as with the case of the slurry used for slip casting.

The method of drying the shaped wet body is not particularly limited, and may be, for example, natural drying, hot-air drying, vacuum drying, dielectric heating, induction heating, or constant-temperature constant-humidity drying. The drying may be achieved by using one of these methods, or two or more of these methods. For advantages such as inhibiting cracking during drying, the preferred drying methods are natural drying, dielectric heating, induction heating, and constant-temperature constant-humidity drying.

(iii) Pressing

In producing a zirconia molded body by the method that includes a step of pressing a powder containing zirconia particles, the pressing is not particularly limited to specific methods, and may be achieved by using a known pressing machine. Specific examples of the pressing method include uniaxial pressing. In order to increase the density of the zirconia molded body produced, it is preferable that uniaxial pressing be followed by cold isostatic pressing (CIP).

The zirconia particle-containing powder used for pressing may additionally contain one or more other components such as above, for example, such as a binder, a plasticizer, a dispersant, an emulsifier, an antifoaming agent, a pH adjuster, and a lubricant. These components may be added at the time of preparing the powder.

(iv) Molding of Resin-Containing Composition

In producing a zirconia molded body by the method that includes a step of molding a composition containing zirconia particles and a resin, the composition molding method is not limited to specific methods, and the composition may be molded by using a method, for example, such as injection molding, cast molding, and extrusion molding. It is also possible to shape the composition using a lamination shaping technique (e.g., 3D printing), for example, such as fused deposition modeling (FDM), an inkjet method, or a powder-binder lamination technique. Preferred as the molding method are injection molding and cast molding, more preferably injection molding.

The resin is not limited to particular types of resins, and resins that function as binders may preferably be used. Specific examples of the resin include fatty acids such as paraffin wax, polyvinyl alcohol, polyethylene, a polypropylene, ethylene-vinyl acetate copolymer, polystyrene, atactic polypropylene, methacrylate resin, and stearic acid. These resins may be used alone, or two or more thereof may be used in combination.

The composition containing zirconia particles and a resin may additionally contain one or more other components such as above, for example, such as a binder, a plasticizer, a dispersant, an emulsifier, an antifoaming agent, a pH adjuster, and a lubricant.

(v) Polymerization of Composition Containing Polymerizable Monomer

Polymerization of the composition containing zirconia particles and a polymerizable monomer can polymerize the polymerizable monomer in the composition, and cure the composition. In producing a zirconia molded body by the method that includes a polymerization step, the method is not particularly limited to specific methods, and may be, for example, (a) a method that polymerizes the zirconia particle- and polymerizable monomer-containing composition in a mold; or (b) stereolithography (SLA) using the composition containing zirconia particles and a polymerizable monomer. Of these, (b) stereolithography is preferred. By stereolithography, a shape corresponding to the shape desired for the product zirconia sintered body can be imparted to the zirconia molded body at the time of its production. This makes the stereolithography a potentially preferred method, particularly when the zirconia sintered body of the present invention is used as a dental material such as a dental prosthesis.

The type of the polymerizable monomer in the zirconia particle- and polymerizable monomer-containing composition is not particularly limited, and the polymerizable monomer may be one selected from monofunctional polymerizable monomers such as monofunctional (meth)acrylates, and monofunctional (meth)acrylamides, and polyfunctional polymerizable monomers such as bifunctional aromatic compounds, bifunctional aliphatic compounds, and tri and higher functional compounds. The polymerizable monomer may be used alone, or two or more thereof may be used. Among these, polyfunctional polymerizable monomers are preferred, particularly when stereolithography is used.

Examples of the monofunctional (meth)acrylates include (meth)acrylates having hydroxyl groups, such as 2-hydroxyethyl(meth)acrylate, 2-hydroxypropyl(meth)acrylate, 3-hydroxypropyl(meth)acrylate, 4-hydroxybutyl(meth)acrylate, 6-hydroxyhexyl(meth)acrylate, 10-hydroxydecyl(meth)acrylate, propylene glycol mono(meth)acrylate, glycerol mono(meth)acrylate, and erythritol mono(meth)acrylate; alkyl(meth)acrylates such as methyl(meth)acrylate, ethyl (meth)acrylate, propyl(meth)acrylate, isopropyl(meth)acrylate, n-butyl(meth)acrylate, sec-butyl(meth)acrylate, t-butyl (meth)acrylate, isobutyl(meth)acrylate, n-hexyl(meth) acrylate, lauryl(meth)acrylate, cetyl(meth)acrylate, and stearyl(meth)acrylate; alicyclic(meth)acrylates, such as cyclohexyl(meth)acrylate, and isobornyl(meth)acrylate; aromatic group-containing(meth)acrylates, such as benzyl (meth)acrylate, and phenyl(meth)acrylate; and (meth)acrylates having functional groups, such as 2,3-dibromopropyl (meth)acrylate, 3-(meth) acryloyloxypropyltrimethoxysilane, and 11-(meth) acryloyloxyundecyltrimethoxysilane.

Examples of the monofunctional (meth)acrylamides include (meth)acrylamide, N-(meth)acryloylmorpholine, N,N-dimethyl(meth)acrylamide, N,N-diethyl(meth)acrylamide, N,N-di-n-propyl(meth)acrylamide, N,N-di-n-butyl (meth)acrylamide, N,N-di-n-hexyl(meth)acrylamide, N,N-di-n-octyl(meth)acrylamide, N,N-di-2-ethylhexyl(meth) acrylamide, N-hydroxyethyl(meth)acrylamide, and N,N-di (hydroxyethyl)(meth)acrylamide.

Among these monofunctional polymerizable monomers, (meth)acrylamides are preferred, and N-(meth)acryloylmorpholine, N,N-dimethyl(meth)acrylamide, and N,N-diethyl (meth)acrylamide are more preferred for their desirable polymerizability.

Examples of the bifunctional aromatic compounds include 2,2-bis((meth)acryloyloxyphenyl)propane, 2,2-bis [4-(3-(meth)acryloyloxy-2-hydroxypropoxy)phenyl]propane, 2,2-bis[4-(3-methacryloyloxy-2-hydroxypropoxy) phenyl]propane (commonly known as "Bis-GMA"), 2,2-bis (4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth) acryloyloxydiethoxyphenyl)-2-(4-(meth) acryloyloxyethoxyphenyl)propane, 2-(4-(meth) acryloyloxythethoxyphenyl)-2-(4-(meth) acryloyloxytriethoxyphenyl)propane, 2-(4-(meth) acryloyloxythpropoxyphenyl)-2-(4-(meth) acryloyloxytriethoxyphenyl)propane, 2,2-bis(4-(meth) acryloyloxypropoxyphenyl)propane, 2,2-bis(4-(meth) acryloyloxyisopropoxyphenyl)propane, and 1,4-bis(2-(meth)acryloyloxyethyl)pyromellitate. Among these, 2,2-bis [4-(3-methacryloyloxy-2-hydroxypropoxy)phenyl]propane ("Bis-GMA"), and 2,2-bis(4-(meth)acryloyloxypolyethoxyphenyl)propane are preferred for their desirable polymerizability and ability to provide desirable strength for the zirconia molded body produced. Preferred as 2,2-bis(4-(meth)acryloyloxypolyethoxyphenyl)propane is 2,2-bis(4-methacryloyloxypolyethoxyphenyl)propane (a compound with an average number of moles of ethoxy group added of 2.6; commonly known as "D-2.6E").

Examples of the bifunctional aliphatic compounds include glycerol di(meth)acrylate, ethylene glycol di(meth) acrylate, diethylene glycol di(meth)acrylate, triethylene glycol di(meth)acrylate, propylene glycol di(meth)acrylate, butylene glycol di(meth)acrylate, neopentyl glycol di(meth) acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanecliol di(meth)acrylate, 1,10-decanediol di(meth)acrylate, 1,2-bis(3-methacryloyloxy-2-hydroxypropoxy)ethane, and 2,2,4-trimethylhexamethylene bis(2-carbamoyloxyethyl)dimethacrylate (commonly known as "UDMA"). Among these, triethylene glycol dimethacrylate (commonly known as "TEGDMA"), and 2,2,4-trimethylhexamethylene bis(2-carbamoyloxyethyl)dimethacrylate are preferred for their desirable polymerizability and ability to provide desirable strength for the zirconia molded body produced.

Examples of the tri and higher functional compounds include trimethylolpropane tri(meth)acrylate, trimethylolethane tri(meth)acrylate, trimethylolmethane tri(meth)acrylate, pentaerythritol tri(meth)acrylate, pentaerythritol tetra (meth)acrylate, dipentaerythritol penta(meth)acrylate, N,N-(2,2,4-trimethylhexamethylene)bis[2-(aminocarboxy) propane-1,3-diol]tetra(meth) acrylate, and 1,7-diacryloyloxy-2,2,6,6-tetra(meth)acryloyloxymethyl-4-oxyheptane. Among these, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane are preferred for their desirable polymerizability and ability to provide desirable strength for the zirconia molded body produced.

Regardless of whether the method (a) or (b) is used, it is preferable that a polymerization initiator be used for the polymerization of the composition, and that the composition contain a polymerization initiator. The type of polymerization initiator is not particularly limited, and the polymerization initiator is particularly preferably a photopolymerization initiator. The photopolymerization initiator may be appropriately selected from photopolymerization initiators commonly used in industry, preferably from photopolymerization initiators used in dentistry. Specific examples of the photopolymerization initiator include those exemplified above in conjunction with gel casting, and are omitted to avoid redundancy.

The composition containing zirconia particles and a polymerizable monomer may additionally contain one or more other components such as above, for example, such as a binder, a plasticizer, a dispersant, an emulsifier, an antifoaming agent, a pH adjuster, and a lubricant.

In producing a zirconia molded body by stereolithography using the composition containing zirconia particles and a polymerizable monomer, the stereolithography is not particularly limited to specific methods, and may be achieved by appropriately using a known method. For example, the desired zirconia molded body may be obtained by forming layers of desired shapes layer-by-layer through photo-polymerization of a liquid composition with, for example, ultraviolet light or a laser, using a stereolithography device.

In obtaining the zirconia molded body by stereolithography, the content of the zirconia particles in the zirconia particle- and polymerizable monomer-containing composition should preferably be as high as possible from the viewpoint of sinterability in a later step. Specifically, the zirconia particle content is preferably 20 mass % or more, more preferably 30 mass % or more, even more preferably 40 mass % or more, particularly preferably 50 mass % or more. From the principle of layer formation in stereolithography, it is preferable that the composition have a viscosity that falls in a certain range. To this end, the content of the zirconia particles in the composition is preferably 90 mass % or less, more preferably 80 mass % or less, even more preferably 70 mass % or less, particularly preferably 60 mass % or less. Adjustment of composition viscosity may be of particular importance when stereolithography is performed using the constrained surface method, in which light is applied upward through the bottom of a container to form a zirconia molded body layer-by-layer, and when the composition needs to be smoothly flown in between the bottom surface of the previously cured layer and the bottom of the container for the formation of the next layer after the cured layer is elevated upward by the height of one layer.

Specifically, the composition has a viscosity of preferably 20,000 mPa·s or less, more preferably 10,000 mPa·s or less, even more preferably 5,000 mPa·s or less, and is preferably 100 mPa·s or more, in terms of a viscosity at 25° C. Because the viscosity of the composition tends to increase with increase of the zirconia particle content, it is preferable to appropriately adjust the balance between zirconia particle content and viscosity in the composition in a way suited for the performance and other characteristics of the stereolithography device, taking into consideration factors such as the balance between the rate of the stereolithography process and the accuracy of the zirconia molded body produced. The viscosity may be measured with an E-type viscometer.

In the method of production of the zirconia molded body of the present invention, a zirconia molded body may be subjected to CIP after being subjected to humidification treatment, to further improve the density of the zirconia molded body. In the case where pressing is carried out, a zirconia particle-containing powder may be pressed after being subjected to humidification treatment. Any known humidification treatment may be used with no limitation. Humidification treatment may be carried out by spraying water with a spray or the like, or by using a hygrostat, thermo-hygrostat, or the like. A moisture content increased by the humidification treatment depends for example on the particle diameter of contained zirconia particles. However, the increased moisture content relative to the mass of powder and a molded body before getting wet is preferably more than 2 mass %, more preferably more than 3 mass %, even more preferably more than 4 mass %, particularly preferably more than 5 mass %, and is preferably 15 mass % or less, more preferably 13 mass % or less, even more preferably 11 mass % or less. Note that the moisture content increased by humidification treatment may be determined as a value in percentage by dividing a value resulting from subtraction of the mass of the powder and the molded body before getting wet from the mass of the powder and the molded body after getting wet, by the mass of the powder and the molded body before getting wet.

Zirconia Pre-Sintered Body

The zirconia pre-sintered body of the present invention comprises: zirconia particles comprising 2.0 to 9.0 mol % yttria and comprising a monoclinic crystal system in a fraction of 55% or more; and 1% or more undissolved yttria, wherein the zirconia pre-sintered body has $\Delta L^*(W-B)$ of 5 or more through a thickness of 1.5 mm. With use of the zirconia pre-sintered body, it is possible to obtain a zirconia sintered body that excels in both translucency and strength and can be produced by short-time sintering.

When producing a zirconia sintered body of the present invention containing a fluorescent agent, it is preferable that the fluorescent agent be contained in the zirconia pre-sintered body. The content of the fluorescent agent in the zirconia pre-sintered body of the present invention may be appropriately adjusted according to, for example, the content of the fluorescent agent in the zirconia sintered body to be produced. Specifically, the content of the fluorescent agent contained in the zirconia pre-sintered body is preferably 0.001 mass % or more, more preferably 0.005 mass % or more, even more preferably 0.01 mass % or more, and is preferably 1 mass % or less, more preferably 0.5 mass % or less, even more preferably 0.1 mass % or less in terms of an oxide of the metallic element contained in the fluorescent agent, relative to the mass of the zirconia contained in the zirconia pre-sintered body.

When producing a zirconia sintered body containing a colorant, it is preferable that the colorant be contained in the zirconia pre-sintered body. The content of the colorant in the zirconia pre-sintered body of the present invention may be appropriately adjusted according to, for example, the content of the colorant in the zirconia sintered body to be produced. Specifically, the content of the colorant in the zirconia pre-sintered body is preferably 0.001 mass % or more, more preferably 0.005 mass % or more, even more preferably 0.01 mass % or more, and is preferably 5 mass % or less, more preferably 1 mass % or less, even more preferably 0.5 mass % or less, and may be 0.1 mass % or less, or 0.05 mass % or less in terms of an oxide of the metallic element contained in the colorant, relative to the mass of the zirconia contained in the zirconia pre-sintered body.

When producing a zirconia sintered body containing a translucency adjuster, it is preferable that the translucency adjuster be contained in the zirconia pre-sintered body. The content of the translucency adjuster in the zirconia pre-sintered body of the present invention may be appropriately adjusted according to, for example, the content of the translucency adjuster in the zirconia sintered body to be produced. Specifically, the content of the translucency adjuster contained in the zirconia pre-sintered body is preferably 0.1 mass % or less relative to the mass of the zirconia contained in the zirconia pre-sintered body.

The yttria content in the zirconia pre-sintered body of the present invention may be the same as that in the zirconia sintered body to be produced, within a range of 2.0 to 9.0 mol %. Specifically, the yttria content in the zirconia pre-sintered body is 2.0 mol % or more, preferably 3.0 mol % or more, more preferably 4.0 mol % or more, and is 9.0 mol % or less, preferably 8.0 mol % or less, more preferably 7.0 mol % or less. It is to be noted that the yttria content in the zirconia pre-sintered body is a fraction (mol %) of the number of moles of yttria with respect to the total number of moles of zirconia and yttria.

The density of the zirconia pre-sintered body of the present invention is not particularly limited, and preferably falls in a range of 3.0 to 6.0 g/m$^3$, more preferably 3.2 to 5.8 g/m$^3$, though the density varies with conditions such as the method of production of the zirconia molded body used for the production of the zirconia pre-sintered body.

The shape of the zirconia pre-sintered body of the present invention is not particularly limited, and may be chosen as desired according to use. However, for example, considering ease of handing of when using the zirconia pre-sintered body as a mill blank for producing a dental material such as a dental prosthesis, the zirconia pre-sintered body preferably has a disc or a prism shape (e.g., rectangular). The zirconia pre-sintered body may be cut (milled) into the desired shape according to use before being formed into a zirconia sintered body, as will be described later. However, the present invention also encompasses zirconia pre-sintered bodies of desired shapes imparted after cutting (milling). The zirconia pre-sintered body may have a monolayer structure or a multilayer structure. However, with a multilayered zirconia pre-sintered body, the resulting zirconia sintered body can have a multilayer structure, which allows translucency and other physical properties to be locally altered.

For advantages such as maintaining the shape of the work in the process of working using a cutting machine, and improving the ease of cutting itself, the three-point flexural strength of the zirconia pre-sintered body of the present invention preferably falls in a range of 10 to 70 MPa, more preferably 20 to 60 MPa. The three-point flexural strength of the zirconia pre-sintered body may be a measured value obtained from a 5 mm×40 mm×10 mm specimen using a multi-purpose tester at a span length of 30 mm and a crosshead speed of 0.5 mm/min.

The zirconia pre-sintered body of the present invention has a crystal grain size of preferably 180 nm or less after being sintered at 900 to 1,200° C. for 10 minutes under ordinary pressure (after being formed into a zirconia sintered body). In this way, the zirconia sintered body of the present invention having excellent translucency can be produced with ease. For advantages such as obtaining a zirconia sintered body having even higher translucency, the crystal grain size is more preferably 140 nm or less, even more preferably 120 nm or less, further even more preferably 115 nm or less, and may be 110 nm or less. The lower limit of crystal grain size is not particularly limited, and the crystal grain size may be, for example, 50 nm or more, or 100 nm or more. The crystal grain size can be measured in the same manner as in the crystal grain size measurement described above in conjunction with the zirconia sintered body.

The zirconia pre-sintered body of the present invention has ΔL*(W–B) of 5 or more, preferably 7 or more, more preferably 10 or more, through a thickness of 1.5 mm. With the ΔL*(W–B) in the range as above, a zirconia sintered body having high linear light transmittance can be obtained after being sintered under ordinary pressure. The upper limit of ΔL*(W–B) is not particularly limited, and may be, for example, 30 or less, or 25 or less. The ΔL*(W–B) of zirconia pre-sintered body through a thickness of 1.5 mm may be measured with a spectrophotometer. For example, a spectrophotometer (CM-3610A manufactured by Konica Minolta Japan) may be used for the measurement. In the measurement, the ΔL*(W–B) may be determined by using F11 as a light source and measuring reflected light. The specimen used for measurement may be a disc-shaped zirconia pre-sintered body measuring 20 mm in diameter and 1.5 mm in thickness.

The zirconia pre-sintered body of the present invention has a three-point flexural strength of 500 MPa or more after being sintered at 900 to 1,200° C. under ordinary pressure (after being formed into a zirconia sintered body). In this way, the zirconia sintered body of the present invention having excellent strength can be produced with ease. For advantages such as obtaining a zirconia sintered body having even higher strength, the three-point flexural strength is preferably 600 MPa or more, more preferably 650 MPa or more, even more preferably 700 MPa or more, particularly preferably 800 MPa or more. In addition, most preferably, the three-point flexural strength after sintering for 10 minutes as the condition of the sintering time satisfies the above range. The upper limit of three-point flexural strength is not particularly limited, and the three-point flexural strength may be, for example, 1,500 MPa or less, or 1,000 MPa or less. The three-point flexural strength can be measured in the same manner as in the measurement of three-point flexural strength described above in conjunction with the zirconia sintered body.

The zirconia pre-sintered body has a transmittance of preferably 40% or more for light of 700 nm wavelength through a thickness of 0.5 mm after being sintered at 900 to 1,200° C. under ordinary pressure (after being formed into a zirconia sintered body). In this way, the zirconia sintered body of the present invention having excellent translucency can be produced with ease. For advantages such as obtaining a zirconia sintered body having even higher translucency, the transmittance is more preferably 45% or more, even more preferably 46% or more, further even more preferably 48% or more, particularly preferably 50% or more, and may be 52% or more. In addition, most preferably, the transmittance for light of 700 nm wavelength through a thickness of 0.5 mm after sintering for 10 minutes as the condition of the sintering time satisfies the above range. The upper limit of transmittance is not particularly limited, and the transmittance may be, for example, 60% or less, or 57% or less. The transmittance can be measured in the same manner as in the measurement of transmittance for light of 700 nm wavelength through a thickness of 0.5 mm described above in conjunction with the zirconia sintered body.

The predominant crystal system of the zirconia pre-sintered body of the present invention is a monoclinic crystal system, and it is important that the zirconia pre-sintered body of the present invention should include the monoclinic crystal system in a fraction $f_m$ of 55% or more with respect to the total amount of the monoclinic crystal system, a tetragonal crystal system, and a cubic crystal system.

For advantages such as ease of obtaining the desired zirconia sintered body, the fraction $f_m$ of the monoclinic crystal system in the zirconia molded body is preferably 60% or more, more preferably 70% or more, even more preferably 80% or more, further more preferably 90% or more, particularly preferably 95% or more with respect to the total amount of the monoclinic crystal system, the tetragonal crystal system, and the cubic crystal system. The fraction $f_m$ of the monoclinic crystal system in the zirconia molded body may be determined by X-ray diffraction (XRD) analysis, using the following formula.

$$f_m = 100 \times I_m / (I_m + I_{t+c})$$

Here, $f_m$ represents the fraction (%) of the monoclinic crystal system with respect to the tetragonal crystal system and the cubic crystal system in the zirconia pre-sintered body, $I_m$ represents the height of a peak (a peak attributed to the (11-1) plane of the monoclinic crystal system) near 2θ=28 degrees, and $I_{t+c}$ represents the height of a peak (a peak attributed to a mixed phase of the (111) plane of the tetragonal crystal system and the (111) plane of the cubic crystal system) near 2θ=30 degrees. When $I_{t+c}$ cannot be easily specified as a result of the peak near 2θ=30 degrees separately appearing as a peak attributed to the (111) plane of the tetragonal crystal system and a peak attributed to the (111) plane of the cubic crystal system, $I_{t+c}$ can be determined as the sum of the height ($I_t$) of the peak attributed to the (111) plane of the tetragonal crystal system and the height ($I_c$) of the peak attributed to the (111) plane of the cubic crystal system.

In the zirconia pre-sintered body of the present invention, yttria is used as a stabilizer. At least a part of the zirconia crystals exists as a monoclinic crystal system by the presence of yttria, and at least a part of yttria is present in an undissolved form in zirconia as a solid solution. It can be confirmed that part of yttria is not dissolved in zirconia as a solid solution for example by an X-ray diffraction (XRD) pattern. The presence of a peak derived from yttria in an XRD pattern of a composition means that the composition contains yttria that is not dissolved in zirconia as a solid solution. A peak derived from yttria is basically not observable in an XRD pattern when yttria has fully dissolved as a solid solution. It is, however, possible, depending on the crystal state or other conditions of yttria, that yttria may not be dissolved in zirconia as a solid solution even when yttria does not produce a peak in the XRD pattern. Yttria can be thought of having dissolved in zirconia as a solid solution mostly, basically completely, when the predominant crystal system of zirconia is a tetragonal crystal system and/or a cubic crystal system and there is no peak attributed to yttria in the XRD pattern. It is to be noted that a stabilizer other than yttria may be used in combination in the present invention.

Preferably, a stabilizer in the zirconia pre-sintered body of the present invention is yttria. In the zirconia pre-sintered body, the fraction $f_y$ of yttria that is not dissolved in zirconia as a solid solution (hereinafter, referred to as "undissolved yttria") is 1% or more, and for advantages such as ease of obtaining the desired zirconia sintered body, the fraction $f_y$ is preferably 2% or more, more preferably 3% or more. The upper limit of the fraction $f_y$ of undissolved yttria depends on the content of yttria in the zirconia pre-sintered body. The fraction $f_y$ may be 15% or less for an yttria content of 7.5 mol % or less with respect to the total mol of zirconia and yttria. For example, the fraction $f_y$ may be 7% or less for an yttria content of 3.5 mol % to 4.5 mol %. The fraction $f_y$ may be 10% or less for an yttria content of 5 mol % to 6 mol %. The fraction $f_y$ may be 11% or less for an yttria content of 5.5 mol % to 6.5 mol %. The fraction $f_y$ of undissolved yttria can be determined using the following formula.

$$f_y = 100 \times I_y / (I_y + I_m + I_{t+c})$$

Here, $f_y$ represents the fraction (%) of undissolved yttria with respect to zirconia in the zirconia pre-sintered body, $I_y$ represents the height of a peak (a peak attributed to the (111) plane of yttria) near 2θ=29 degrees, $I_m$ represents the height of a peak (a peak attributed to the (11-1) plane of the monoclinic crystal system) near 2θ=28 degrees, and $I_{t+c}$ represents the height of a peak (a peak attributed to a mixed phase of the (111) plane of the tetragonal crystal system and the (111) plane of the cubic crystal system) near 2θ=30 degrees. When $I_{t+c}$ cannot be easily specified as a result of the peak near 2θ=30 degrees separately appearing as a peak attributed to the (111) plane of the tetragonal crystal system and a peak attributed to the (111) plane of the cubic crystal system, $I_{t+c}$ can be determined as the sum of the height ($I_t$) of the peak attributed to the (111) plane of the tetragonal crystal system and the height ($I_c$) of the peak attributed to the (111) plane of the cubic crystal system. Also, when a stabilizer other than yttria is used in combination, the above formula is applicable to calculation of the percentage presence of undissolved stabilizer other than yttria by substituting a peak of the other stabilizer for $I_y$.

The zirconia pre-sintered body of the present invention has a linear light transmittance of preferably 1% or more, more preferably 3% or more, even more preferably 5% or more, further even more preferably 7% or more, and may be 10% or more, through a thickness of 1.0 mm after being sintered at 900 to 1,200° C. for 10 minutes under ordinary pressure (after being formed into a zirconia sintered body). With the linear light transmittance falling in these ranges, the zirconia sintered body can more easily satisfy the level of translucency required for the incisal region when used as, for example, a dental prosthesis. The upper limit of linear light transmittance is not particularly limited, and the linear light transmittance may be, for example, 60% or less, or 50% or less. The linear light transmittance can be measured in the same manner as in the measurement of linear light transmittance through a thickness of 1.0 mm described above in conjunction with the zirconia sintered body.

Method of Production of Zirconia Pre-sintered Body

The method of production of the zirconia pre-sintered body of the present invention is, for example, a method comprising using the zirconia molded body of the present invention, and preferably includes a step of pre-sintering the zirconia molded body at 200° C. or more and less than 800° C. For advantages such as ease of obtaining the desired zirconia pre-sintered body, the pre-sintering temperature is preferably 200° C. or more, more preferably 250° C. or more, even more preferably 300° C. or more, and is preferably 800° C. or less, more preferably 700° C. or less, even more preferably 600° C. or less. With a pre-sintering temperature equal to or greater than the foregoing lower limits, it is possible to effectively inhibit generation of organic material residues. With a pre-sintering temperature equal to or less than the foregoing upper limits, it is possible to reduce the difficulty in cutting (milling) with a cutting machine occurring when the sintering overly proceeds.

The rate of temperature increase in pre-sintering of the zirconia molded body of the present invention is not particularly limited, and is preferably 0.1° C./min or more, more preferably 0.2° C./min or more, even more preferably 0.5° C./min or more, and is preferably 50° C./min or less, more preferably 30° C./min or less, even more preferably 20° C./min or less. The productivity improves when the rate of temperature increase is equal to or greater than the foregoing lower limits. With a rate of temperature increase equal to or less than the foregoing upper limits, it is possible to reduce the volume difference between inner and outer portions of the zirconia molded body and the zirconia pre-sintered body, and to reduce cracking and breakage by inhibiting the organic materials from undergoing rapid decomposition when the zirconia molded body is containing organic materials.

The pre-sintering time in the pre-sintering of the zirconia molded body of the present invention is not particularly limited. However, for advantages such as efficiently and stably obtaining the desired zirconia pre-sintered body with good productivity, the pre-sintering time is preferably 0.5 hours or more, more preferably 1 hour or more, even more preferably 2 hours or more, and is preferably 10 hours or less, more preferably 8 hours or less, even more preferably 6 hours or less.

Pre-sintering in the present invention may be carried out using a pre-sintering furnace. The type of pre-sintering furnace is not particularly limited, and the pre-sintering furnace may be, for example, an electric furnace or a debinding furnace commonly used in industry.

The zirconia pre-sintered body of the present invention may be cut (milled) into the desired shape according to use, before being formed into a zirconia sintered body. To describe more specifically, the zirconia sintered body of the present invention excels in both translucency and strength despite containing a fluorescent agent, and is particularly preferred as, for example, a dental material such as a dental prosthesis. To this end, the zirconia pre-sintered body may be cut (milled) into a shape corresponding to the shape of such a material so that a zirconia sintered body for use in such applications can be obtained. Cutting (milling) is not limited to specific methods, and may be achieved by using, for example, a known milling device.

Method of Production of Zirconia Sintered Body

As described above, the zirconia sintered body of the present invention can be produced by sintering the zirconia molded body of the present invention under ordinary pressure, and also can be produced by sintering the zirconia pre-sintered body of the present invention under ordinary pressure.

For advantages such as ease of obtaining the desired zirconia sintered body, the sintering temperature is preferably 900° C. or more, more preferably 1,000° C. or more, even more preferably 1,050° C. or more, and also for advantages such as ease of obtaining the desired zirconia sintered body, the sintering temperature is preferably 1,200° C. or less, more preferably 1,150° C. or less, even more preferably 1,120° C. or less, regardless of whether the zirconia molded body of the present invention or the zirconia pre-sintered body of the present invention is sintered. With a sintering temperature equal to or greater than the foregoing lower limits, sintering can sufficiently proceed, and a compact sintered body can be obtained with ease. With a sintering temperature equal to or less than the foregoing upper limits, it is possible to easily obtain a zirconia sintered body having a crystal grain size within the ranges of the present invention, and to inhibit deactivation of fluorescent agent.

In sintering the zirconia molded body of the present invention and the zirconia pre-sintered body of the present invention, the sintering time is not particularly limited; however, for advantages such as efficiently and stably obtaining the desired zirconia sintered body with good productivity, the sintering time is preferably 5 minutes or more, more preferably 8 minutes or more, even more preferably 10 minutes or more, and is preferably 6 hours or less, more preferably 4 hours or less, even more preferably 2 hours or less, regardless of whether the zirconia molded body of the present invention or the zirconia pre-sintered body of the present invention is sintered. The sintering time may be 1 hour or less or 30 minutes or less.

Sintering in the present invention may be carried out using a sintering furnace. The type of sintering furnace is not particularly limited, and the sintering furnace may be, for example, an electric furnace or a debinding furnace commonly used in industry. Specifically, when the zirconia sintered body is to be used for dental material applications, it is possible to use a dental porcelain furnace, which operates in a relatively low sintering temperature range, other than using a traditional dental sintering furnace for zirconia.

The zirconia sintered body of the present invention can be produced with ease without HIP. However, further improvement of translucency and strength can be achieved when the sintering under ordinary pressure is followed by HIP.

Use of Zirconia Sintered Body

The zirconia sintered body of the present invention is not limited to particular applications. However, because the zirconia sintered body of the present invention excels in both translucency and strength and can be produced by short-time sintering, the zirconia sintered body of the present invention is particularly preferred as a dental material such as a dental prosthesis, and is highly useful not only as a dental prosthesis for the cervical region of a tooth, but as a dental prosthesis for the occlusal surface of a posterior tooth, and the incisal region of a front tooth. The zirconia sintered body of the present invention is particularly preferred for use as a dental prosthesis for the incisal region of a front tooth.

EXAMPLES

The following describes the present invention in greater detail using Examples and Comparative Examples. It is to be noted, however, that the present invention is not limited by the following descriptions. The methods used to measure physical properties are as follows.

(1) Average Primary Particle Diameter of Zirconia Particles

The average primary particle diameter of zirconia particles was determined by taking a micrograph of zirconia particles with a transmission electron microscope (TEM), and finding a mean value of particle diameters (maximum diameters) measured for arbitrarily chosen 100 particles from the photographed image.

(2) Fraction of Particles having Particle Diameter of More Than 100 nm

Zirconia particles were dispersed in methanol and measurement was performed with a laser diffraction/scattering particle size distribution analyzer (LA-950 manufactured by Horiba Ltd.).

(3) Crystal Grain Size

The crystal grain size of zirconia sintered body was determined by taking a micrograph of zirconia sintered body cross sections with a field emission scanning electron microscope (FE-SEM), and finding a mean value of diameters of circles corresponding to 10 arbitrarily selected particles from the micrograph (the diameters of true circles having the same areas as these particles).

(4) Three-Point Flexural Strength

The three-point flexural strength of zirconia sintered body was measured in compliance with ISO 6872:2015. A specimen measuring 4 mm×1.2 mm×15 mm in size was produced from a plate-shaped zirconia sintered body of each of Examples and Comparative Examples, and the measurement was performed on the specimen with a multi-purpose tester at a span length of 12 mm and a crosshead speed of 0.5 mm/min.

(5) Light Transmittance (700 nm Wavelength, 0.5 mm Thickness)

The transmittance of zirconia sintered body for light of 700 nm wavelength through a thickness of 0.5 mm was measured with an integrating sphere by measuring light from a light source passing and scattering on a specimen, using a spectrophotometer (Hitachi spectrophotometer, Model U-3900H manufactured by Hitachi High-Technologies Corporation). In the measurement, the transmittance for light of 700 nm wavelength was determined after measuring transmittance in a wavelength region of 300 to 750 nm. For the measurement, a disc-shaped zirconia sintered body having mirror polished surfaces and measuring 15 mm in diameter and 0.5 mm in thickness was used as a specimen.

(6) Linear Light Transmittance (1.0 mm Thickness)

The linear light transmittance of zirconia sintered body through a thickness of 1.0 mm was measured with an integrating sphere by measuring light from a light source passing and scattering on a specimen, using a turbidimeter (Haze Meter NDH 4000 manufactured by Nippon Denshoku Industries Co., Ltd.). In the measurement, the linear light transmittance was measured in compliance with ISO 13468-1:1996 and JIS K 7361-1:1997, and the haze was measured in compliance with ISO 14782-1:1999 and JIS K 7136:2000. For the measurement, a disc-shaped zirconia sintered body having mirror polished surfaces and measuring 15 mm in diameter and 1.0 mm in thickness was used as a specimen.

(7) Fraction of Monoclinic Crystal System in Zirconia Molded Body and Pre-Sintered Body The fraction $f_m$ of the monoclinic crystal system in the zirconia molded body and pre-sintered body was determined by X-ray diffraction (XRD) analysis, using the following formula.

$$f_m = 100 \times I_m/(I_m + I_t + I_c)$$

Here, $f_m$ represents the fraction (%) of the cubic crystal system with respect to the tetragonal crystal system and the cubic crystal system in the zirconia molded body and pre-sintered body, $I_m$ represents the height of a peak (a peak attributed to the (11-1) plane of a monoclinic crystal system) near 2θ=28 degrees, $I_t$ represents the height of a peak (a peak attributed to the (111) plane of a tetragonal crystal system) near 2θ=30 degrees, and $I_c$ represents the height of a peak (a peak attributed to the (111) plane of the cubic crystal system) near 2θ=30 degrees. For the measurement, disc-shaped zirconia molded bodies and pre-sintered bodies of Examples and Comparative Examples were used as specimens.

(8) Fraction of Undissolved Yttria in Zirconia Molded Body and Pre-Sintered Body The fraction $f_y$ of undissolved yttria in the zirconia molded body and pre-sintered body was determined by X-ray diffraction (XRD) analysis, using the following formula.

$$f_y=100\times I_y/(I_y+I_m+I_t+I_c)$$

Here, $f_y$ represents the fraction (%) of undissolved yttria with respect to zirconia in the zirconia molded body and pre-sintered body, $I_y$ represents the height of a peak (a peak attributed to the (111) plane of yttria) near 2θ=29 degrees, $I_m$ represents the height of a peak (a peak attributed to the (11-1) plane of the monoclinic crystal system) near 2θ=28 degrees, $I_t$ represents the height of a peak (a peak attributed to the (111) plane of the tetragonal crystal system) near 2θ=30 degrees, and $I_c$ represents the height of a peak (a peak attributed to the (111) plane of the cubic crystal system) near 2θ=30 degrees. For the measurement, disc-shaped zirconia molded bodies and pre-sintered bodies of Examples and Comparative Examples were used as specimens.

(9) Fraction of Monoclinic Crystal System After Hot-Water Treatment

The fraction of monoclinic crystal system with respect to tetragonal crystal system and cubic crystal system after the zirconia sintered body is immersed in 180° C. hot water for 5 hours was determined by mirror polishing a surface of the zirconia sintered body, and measuring the mirror polished surface portion by X-ray diffraction (XRD) analysis after the zirconia sintered body was immersed in 180° C. hot water for 5 hours, using the following formula.

$$f_m=100\times I_m/(I_{t+c})$$

Here, $f_m$ represents the fraction (%) of the monoclinic crystal system with respect to the tetragonal crystal system and the cubic crystal system in the zirconia sintered body immersed in 180° C. hot water for 5 hours, $I_m$ represents the height of a peak (a peak attributed to the (11-1) plane of the monoclinic crystal) near 2θ=28 degrees, and $I_{t+c}$ represents the height of a peak (a peak attributed to a mixed phase of the (111) plane of the tetragonal crystal system and the (111) plane of the cubic crystal system) near 2θ=30 degrees. For the measurement, disc-shaped sintered bodies of Examples and Comparative Examples were used as specimens.

(10) Appearance of Zirconia Sintered Body

The appearance (color) of zirconia sintered body was evaluated by visual inspection.

(11) Fluorescence of Zirconia Sintered Body

For evaluation of the fluorescence of zirconia sintered body, the presence or absence of fluorescence under UV light was determined by visual inspection.

(12) ΔL*(W−B) of Zirconia Molded Body and Zirconia Pre-Sintered Body

The ΔL*(W−B) of zirconia molded body and zirconia pre-sintered body through a thickness of 1.5 mm was measured with a spectrophotometer. Specifically, the ΔL*(W−B) was measured with a spectrophotometer (CM-3610A manufactured by Konica Minolta Japan, Inc.), and calculated with color management software SpectraMagic NX ver. 2.5 manufactured by Konica Minolta Co., Ltd. In the measurement, the ΔL*(W−B) was determined by using F11 as a light source and measuring reflected light. For the measurement, disc-shaped zirconia molded body and zirconia pre-sintered body each having mirror polished surfaces and measuring 20 mm in diameter and 1.5 mm in thickness were used as specimens.

Example 1

A 1.0-L aqueous solution of 0.62 mol/L zirconium oxychloride, a 1.0-L aqueous solution of 0.038 mol/L yttrium chloride, and two pieces of a 0.5-L aqueous solution of 1.9 mol/L sodium hydroxide were separately prepared.

Two precipitation vessels were prepared, and 1.0 L of purified water was poured into each of the precipitation vessels. Further, while a zirconium chloride aqueous solution and a sodium hydroxide aqueous solution were simultaneously poured into one of the precipitation vessels, yttrium chloride and a sodium hydroxide aqueous solution were simultaneously poured into the other precipitation vessel, to obtain respective slurries through precipitation of zirconium oxychloride and yttrium chloride.

After these slurries were filtered and washed, 22.2 g of acetic acid was added to each of the slurries and a hydrothermal treatment was conducted at 200° C. for 3 hours. The slurries thus obtained were subjected to centrifugal filtration with a membrane filter having a pore diameter of 100 nm, and purified water was added so that solid contents (respective concentrations of zirconia and yttria) were 5.0 mass %, to produce a zirconia slurry and an yttria slurry from which coarse particles have been removed. The yttria slurry of 0.5 L was gradually dropped in the zirconia slurry of 0.5 L at a rate of 10 mL/min at room temperature to obtain a mixed slurry of 1 L. The particles contained in the mixed slurry had an average primary particle diameter of 15 nm, and were not to confirmed to include particles having a particle diameter of more than 100 nm.

The mixed slurry was poured as a molding slurry into a plaster mold and allowed to stand for 2 weeks at room temperature, and then was subjected to cold isostatic pressing (CIP) (170 MPa pressure) to obtain zirconia molded bodies of increased density. The plaster mold was prepared so that a molded body before being subjected to CIP had a plate shape measuring 25 mm×25 mm×5 mm in size and a disc shape measuring 20 mm in diameter and 2.5 mm in thickness. The plaster mold was prepared by mixing water into a plaster (Noritake Dental Plaster manufactured by Kuraray Noritake Dental Inc.) in a proportion of 50 mass %. The zirconia molded body was pre-sintered at 500° C. for 2 hours under ordinary pressure to obtain a zirconia pre-sintered body. Further, the zirconia pre-sintered body was sintered at 1,100° C. for 10 minutes under ordinary pressure to obtain a zirconia sintered body containing 3 mol % yttria. The obtained zirconia sintered body was white in color. The measurement results are presented in Table 1.

The zirconia pre-sintered body produced in the manner described above was cut into shapes of crowns for maxillary central incisor and mandibular first molar using a milling device (Katan a H-18 manufactured by Kuraray Noritake Dental Inc.). These were then sintered at 1,100° C. for 10 minutes under ordinary pressure to obtain crown-shaped dental prostheses.

Example 2

A mixed slurry was produced in the same manner as in Example 1, except that an aqueous solution containing 0.62 mol/L zirconium oxychloride and an aqueous solution containing 0.066 mol/L yttrium chloride were used in place of the aqueous solutions used in Example 1. The particles contained in the mixed slurry had an average primary particle diameter of 17 nm, and included 0.20 mass % particles having a particle diameter of more than 100 nm.

A zirconia molded body, a zirconia pre-sintered body, and a zirconia sintered body each containing 5 mol % yttria were obtained in the same manner as in Example 1, except that the mixed slurry obtained above was used as a molding slurry. The obtained zirconia sintered body was white in color. The measurement results are presented in Table 1.

Example 3

A mixed slurry was produced in the same manner as in Example 1, except that an aqueous solution containing 0.62 mol/L zirconium oxychloride and an aqueous solution containing 0.108 mol/L yttrium chloride were used in place of the aqueous solutions used in Example 1. The particles contained in the mixed slurry had an average primary particle diameter of 19 nm, and included 0.40 mass % particles having a particle diameter of more than 100 nm. A zirconia molded body, a zirconia pre-sintered body, and a zirconia sintered body each containing 8 mol % yttria were obtained in the same manner as in Example 1, except that the mixed slurry was used as a molding slurry. The obtained zirconia sintered body was white in color. The measurement results are presented in Table 1.

Example 4

A molding slurry containing zirconia particles and a fluorescent agent was prepared by adding a dilute nitric acid solution of bismuth nitrate to the mixed slurry prepared in Example 2 (having an average primary particle diameter of 17 nm and including 0.20 mass % particles having a particle diameter of more than 100 nm) so that the resulting mixture had a concentration of 0.02 mass % in terms of an oxide of bismuth ($Bi_2O_3$) relative to the mass of zirconia.

A zirconia molded body, a zirconia pre-sintered body, and a zirconia sintered body each containing 5 mol % yttria were obtained in the same manner as in Example 1, except that the molding slurry prepared above was used. The zirconia sintered body obtained was white in color, and had fluorescence. The measurement results are presented in Table 1.

Example 5

A molding slurry containing zirconia particles and a colorant was prepared by adding an aqueous solution of nickel(II) nitrate to the mixed slurry prepared in Example 2 (having an average primary particle diameter of 17 nm and including 0.20 mass % particles having a particle diameter of more than 100 nm) so that the resulting mixture had a concentration of 0.02 mass % in terms of an oxide of nickel(II) (NiO) relative to the mass of zirconia.

A zirconia molded body, a zirconia pre-sintered body, and a zirconia sintered body each containing 5 mol % yttria were obtained in the same manner as in Example 1, except that the molding slurry prepared above was used. The zirconia sintered body obtained was red in color. The measurement results are presented in Table 1.

Comparative Example 1

By uniaxial pressing, a zirconia particle powder TZ-3Y (manufactured by Tosoh Corporation, tetragonal crystal system, yttria content of 3 mol %, average primary particle diameter of 30 nm) was formed into a plate shape measuring 25 mm×25 mm×5 mm in size, and a disc shape measuring 20 mm in diameter and 2.5 mm in thickness. These were subjected to cold isostatic pressing (CIP, 170 MPa pressure) to obtain zirconia molded bodies of increased density. These zirconia molded bodies were pre-sintered at 500° C. for 2 hours under ordinary pressure to obtain zirconia pre-sintered bodies. Further, the zirconia pre-sintered bodies were sintered at 1,100° C. for 10 minutes under ordinary pressure to obtain a zirconia sintered body containing 3 mol % yttria. The obtained zirconia sintered body was white in color. The measurement results are presented in Table 1.

Comparative Example 2

The zirconia molded body produced in Comparative Example 1 was pre-sintered at 500° C. for 2 hours under ordinary pressure to obtain zirconia pre-sintered bodies. Further, the zirconia pre-sintered bodies were sintered at 1,100° C. for 2 hours under ordinary pressure to obtain a zirconia sintered body containing 3 mol % yttria. The obtained zirconia sintered body was white in color. The measurement results are presented in Table 1.

Comparative Example 3

The zirconia molded body produced in Comparative Example 1 was pre-sintered at 500° C. for 2 hours under ordinary pressure to obtain zirconia pre-sintered bodies. Further, the zirconia pre-sintered bodies were sintered at 1,500° C. for 2 hours under ordinary pressure to obtain a zirconia sintered body containing 3 mol % yttria. The obtained zirconia sintered body was white in color. The measurement results are presented in Table 1.

Comparative Example 4

A 1.0-L mixed aqueous solution of 0.62 mol/L zirconium oxychloride and 0.066 mol/L yttrium chloride, and 0.5 L of a 1.9 mol/L aqueous solution of sodium hydroxide were separately prepared.

After pouring 1.0 L of purified water into a precipitation vessel, the mixed aqueous solution and the sodium hydroxide aqueous solution were simultaneously poured into the vessel to obtain a slurry through coprecipitation of zirconium oxychloride and yttrium chloride.

After the slurry was filtered and washed, 22.2 g of acetic acid was added to the slurry and a hydrothermal treatment was conducted at 200° C. for 3 hours. The slurry thus obtained was subjected to centrifugal filtration with a membrane filter having a pore diameter of 100 nm, and purified water was added so that a solid content (a concentration of zirconia and yttria) was 5.0 mass %, to produce a zirconia slurry from which coarse particles have been removed. The zirconia particles contained in the zirconia slurry had an average primary particle diameter of 18 nm, and included 0.35 mass % zirconia particles having a particle diameter of more than 100 nm.

The zirconia slurry was poured as a molding slurry into a plaster mold and allowed to stand for 2 weeks at room temperature, and then was subjected to cold isostatic pressing (CIP) (170 MPa pressure) to obtain zirconia molded bodies of increased density. The plaster mold was prepared so that a molded body before being subjected to CIP had a plate shape measuring 25 mm×25 mm×5 mm in size and a disc shape measuring 20 mm in diameter and 2.5 mm in thickness. The plaster mold was prepared by mixing water into a plaster (Noritake Dental Plaster manufactured by Kuraray Noritake Dental Inc.) in a proportion of 50 mass %. The zirconia molded body was pre-sintered at 500° C. for 2 hours under ordinary pressure to obtain a zirconia pre-sintered body. Further, the zirconia pre-sintered body was sintered at 1,100° C. for 10 minutes under ordinary pressure to obtain a zirconia sintered body containing 5 mol % yttria. The obtained zirconia sintered body was white in color. The measurement results are presented in Table 1.

molding slurry containing zirconia particles, a pH adjuster, a dispersant, and a gelatinizer.

The molding slurry was poured into a polypropylene mold, and dried at room temperature for 16 days to obtain a zirconia molded body. The zirconia molded body was pre-sintered at 500° C. for 2 hours under ordinary pressure to obtain a zirconia pre-sintered body. Further, the zirconia pre-sintered body was sintered at 1,100° C. for 10 minutes under ordinary pressure to obtain a zirconia sintered body containing 5 mol % yttria. The obtained zirconia sintered body was white in color. The measurement results are presented in Table 2.

Example 7

To the mixed slurry prepared in Example 2 (having an average primary particle diameter of 17 nm and including 0.20 mass % zirconia particles having a particle diameter of more than 100 nm), a dispersion medium replacement procedure was applied in which 50 parts by mass of 2-ethoxyethanol was added, and concentrated to make the total amount 100 parts by mass, using a rotary evaporator.

TABLE 1

|  |  | Example | | | | | Comparative Example | | | |
| --- | --- | --- | --- | --- | --- | --- | --- | --- | --- | --- |
|  |  | 1 | 2 | 3 | 4 | 5 | 1 | 2 | 3 | 4 |
| Content of fluorescent agent (*1) | mass % | — | — | — | 0.02 | — | — | — | — | — |
| Content of colorant (*1) | mass % | — | — | — | — | 0.02 | — | — | — | — |
| Content of yttria (*2) | mol % | 3 | 5 | 8 | 5 | 5 | 3 | 3 | 3 | 5 |
| Zirconia molded body |  |  |  |  |  |  |  |  |  |  |
| ΔL*(W − B) | — | 7.8 | 14.1 | 16.2 | 13.1 | 13.6 | 0 | 0 | 0 | 14.3 |
| Fraction of monoclinic crystal | % | 100 | 100 | 100 | 100 | 100 | 20 | 20 | 20 | 0 |
| Fraction of undissolved yttria | % | 4.2 | 7.1 | 11.0 | 7.1 | 7.0 | 0 | 0 | 0 | 0 |
| Zirconia pre-sintered body |  |  |  |  |  |  |  |  |  |  |
| ΔL*(W − B) | — | 6.3 | 13.8 | 15.0 | 12.1 | 12.7 | 0 | 0 | 0 | 13.9 |
| Fraction of monoclinic crystal | % | 95 | 93 | 98 | 93 | 92 | 20 | 20 | 20 | 0 |
| Fraction of undissolved yttria | % | 3.9 | 7.0 | 10.5 | 6.9 | 6.8 | 0 | 0 | 0 | 0 |
| Zirconia sintered body |  |  |  |  |  |  |  |  |  |  |
| Crystal grain size | nm | 81 | 80 | 88 | 81 | 83 | 89 | 107 | 520 | 72 |
| Three-point flexural strength | MPa | 1005 | 805 | 589 | 798 | 813 | 47 | 121 | 1172 | 430 |
| Light transmittance (700 nm wavelength, 0.5 mm thickness) | % | 41 | 47 | 53 | 41 | 43 | 0 | 0 | 21 | 37 |
| Linear light transmittance (1.0 mm thickness) | % | 1.7 | 8.8 | 12.2 | 6.2 | 6.8 | 0 | 0 | 0.4 | 0.3 |
| Fraction of cubic crystal | % | 31 | 100 | 100 | 100 | 100 | 0 | 0 | 31 | 87 |
| Fraction of monoclinic crystal after hot-water treatment | % | 0 | 0 | 0 | 0 | 0 | 0 | 0 | 0 | 0 |

(*1) Content relative to the mass of zirconia (the content is in terms of an oxide of metallic element)
(*2) Fraction of the number of moles of yttria with respect to the total number of moles of zirconia and yttria Example 6

To the mixed slurry prepared in Example 2 (having an average primary particle diameter of 17 nm and including 0.20 mass % zirconia particles having a particle diameter of more than 100 nm), tetramethylammonium hydroxide was added as a pH adjuster and triammonium citrate was added as a dispersant. Thereafter, agarose was added as a gelatinizer while stirring the mixture under heat to produce a The dispersion medium replacement procedure was repeated 4 times to produce a 2-ethoxyethanol-replaced slurry. The 2-ethoxyethanol-replaced slurry had a residual moisture content of 0.06 mass % as measured with a Karl Fisher moisture content meter.

The 2-ethoxyethanol-replaced slurry was dried with a spray drier (B-290 manufactured by Buchi Labortechnik AG, Japan) at a feed rate of 5 mL/min and inlet and outlet temperatures of 150° C. and 100° C., respectively, to obtain a powder containing zirconia particles.

By uniaxial pressing, the powder was formed into a plate shape measuring 25 mm×25 mm×5 mm in size, and a disc shape measuring 20 mm in diameter and 2.5 mm in thickness. These were then subjected to cold isostatic pressing (CIP) (170 MPa pressure) to obtain zirconia molded bodies of increased density. These zirconia molded bodies were pre-sintered at 500° C. for 2 hours under ordinary pressure to obtain zirconia pre-sintered bodies. Further, the zirconia pre-sintered bodies were sintered at 1,100° C. for 10 minutes under ordinary pressure to obtain a zirconia sintered body containing 5 mol % yttria. The obtained zirconia sintered body was white in color. The measurement results are presented in Table 2.

The zirconia pre-sintered body produced in the manner described above was cut into shapes of crowns for maxillary central incisor and mandibular first molar using a milling device (Katana H-18 manufactured by Kuraray Noritake Dental Inc.). These were then sintered at 1,100° C. for 10 minutes under ordinary pressure to obtain crown-shaped dental prostheses.

Example 8

To the zirconia slurry prepared in Example 2 (having an average primary particle diameter of 17 nm and including 0.20 mass % zirconia particles having a particle diameter of more than 100 nm), isopropanol was added in 9 times the volume of the zirconia slurry. The mixture was placed in a centrifuge tube, thoroughly mixed, and centrifuged at 4,000 rpm for 10 minutes. After confirming sedimentation of a white substance, the supernatant was removed, and isopropanol was added again. The mixture was thoroughly mixed, and centrifuged at 4,000 rpm for 10 minutes. The supernatant was removed after confirming sedimentation of a white substance, and methanol was added to make the volume of the mixture the same as the volume of the zirconia slurry used. The mixture was then thoroughly mixed to produce a methanol-replaced slurry. The methanol-replaced slurry had a residual moisture content of 0.05 mass % as measured with a Karl Fisher moisture content meter.

The methanol-replaced slurry produced was subjected to supercritical drying with a supercritical drier using the following procedure. Specifically, the methanol-replaced slurry was placed in a pressure vessel, and the pressure vessel was coupled to a supercritical carbon dioxide extraction device. After checking that there is no pressure leak, the pressure vessel, with a preheating tube, was immersed in a water bath that had been heated to 60° C. The slurry was then allowed to stand for 10 minutes to stabilize after being heated to 80° C. and pressurized to 25 MPa. Thereafter, carbon dioxide and entrainer methanol were introduced under predetermined conditions (temperature: 80° C., pressure: 25 MPa, carbon dioxide flow rate: 10 mL/min, entrainer (methanol) flow rate: 1.5 mL/min). The feeding of methanol was discontinued after an elapsed time period of 2 hours, without stopping the carbon dioxide feed. After 2 hours with the sole supply of carbon dioxide, the feeding of carbon dioxide was stopped, and the pressure was gradually brought back to ordinary pressure from 25 MPa over a time period of about 20 minutes at a maintained temperature of 80° C. The pressure vessel was then taken out of the water bath, and cooled to ordinary temperature. The processed specimen was collected by opening the container, and a powder containing zirconia particles was obtained.

A zirconia molded body, a zirconia pre-sintered body, and a zirconia sintered body each containing 5 mol % yttria were obtained in the same manner as in Example 7, except that the powder obtained above was used. The obtained zirconia sintered body was white in color. The measurement results are presented in Table 2.

Example 9

To the zirconia slurry prepared in Example 2 (having an average primary particle diameter of 17 nm and including 0.20 mass % zirconia particles having a particle diameter of more than 100 nm), isopropanol was added in 9 times the volume of the zirconia slurry. The mixture was placed in a centrifuge tube, thoroughly mixed, and centrifuged at 4,000 rpm for 10 minutes. After confirming sedimentation of a white substance, the supernatant was removed, and isopropanol was added again. The mixture was thoroughly mixed, and centrifuged at 4,000 rpm for 10 minutes. The supernatant was removed after confirming sedimentation of a white substance, and tert-butyl alcohol was added to make the volume of the mixture the same as the volume of the zirconia slurry used. The mixture was then thoroughly mixed to produce a tert-butyl alcohol-replaced slurry. The tert-butyl alcohol-replaced slurry had a residual moisture content of 0.04 mass % as measured with a Karl Fisher moisture content meter.

The tert-butyl alcohol-replaced slurry was transferred to an aluminum vat, and immersed in liquid nitrogen in a separately prepared Dewar flask to freeze. The frozen tert-butyl alcohol-replaced slurry was allowed to stand in a freeze drier that had been precooled to −40° C. The pressure inside the freeze drier was then reduced to 130 Pa or less with a vacuum pump to bring the temperature inside the freeze drier to −10° C. The internal temperature of the freeze drier was confirmed by inserting temperature sensors inside and outside of the aluminum vat. After the temperature inside the freeze drier had stabilized at −10° C. for 72 hours, the temperature difference inside and outside of the aluminum vat was confirmed to be within 5° C., and the temperature inside the freeze drier was brought to 30° C. After being allowed to stand for 24 hours, the inside of the freeze drier was released from the reduced pressure to obtain a powder containing zirconia particles.

A zirconia molded body, a zirconia pre-sintered body, and a zirconia sintered body each containing 5 mol % yttria were obtained in the same manner as in Example 7, except that the powder obtained above was used. The obtained zirconia sintered body was white in color. The measurement results are presented in Table Example 10

A 1.0-L mixed aqueous solution of 0.62 mol/L zirconium oxychloride and 0.066 mol/L yttrium chloride, and 0.5 L of a 1.9 mol/L aqueous solution of sodium hydroxide were separately prepared.

After pouring 1.0 L of purified water into a precipitation vessel, the mixed aqueous solution and the sodium hydroxide aqueous solution were simultaneously poured into the vessel to obtain a slurry through coprecipitation of zirconium oxychloride and yttrium chloride.

After the slurry was filtered and washed, 22.2 g of acetic acid was added to the slurry and a hydrothermal treatment was conducted at 200° C. for 30 minutes. The slurry thus obtained was subjected to centrifugal filtration with a membrane filter having a pore diameter of 100 nm, and purified water was added so that a solid content (a concentration of zirconia and yttria) was 5.0 mass %, to produce a zirconia slurry from which coarse particles have been removed. The zirconia particles contained in the zirconia slurry had an average primary particle diameter of 18 nm, and included 0.32 mass % zirconia particles having a particle diameter of more than 100 nm.

The zirconia slurry was poured as a molding slurry into a plaster mold and allowed to stand for 2 weeks at room temperature, and then was subjected to cold isostatic pressing (CIP) (170 MPa pressure) to obtain zirconia molded bodies of increased density. The plaster mold was prepared so that a molded body before being subjected to CIP had a plate shape measuring 25 mm×25 mm×5 mm in size and a disc shape measuring 20 mm in diameter and 2.5 mm in thickness. The plaster mold was prepared by mixing water into a plaster (Noritake Dental Plaster manufactured by Kuraray Noritake Dental Inc.) in a proportion of 50 mass %.

After the slurry was filtered and washed, 22.2 g of acetic acid was added to the slurry and a hydrothermal treatment was conducted at 200° C. for 1 hour. The slurry thus obtained was subjected to centrifugal filtration with a membrane filter having a pore diameter of 100 nm, and purified water was added so that a solid content (a concentration of zirconia and yttria) was 5.0 mass %, to produce a zirconia slurry from which coarse particles have been removed. The zirconia particles contained in the zirconia slurry had an average primary particle diameter of 17 nm, and included 0.28 mass % zirconia particles having a particle diameter of more than 100 nm.

A zirconia molded body, a zirconia pre-sintered body, and a zirconia sintered body each containing 5 mol % yttria were obtained in the same manner as in Example 10, except that the zirconia slurry obtained above was used as a molding slurry. The obtained zirconia sintered body was white in color. The measurement results are presented in Table 2.

TABLE 2

|  |  | Example | | | | | |
| --- | --- | --- | --- | --- | --- | --- | --- |
|  |  | 6 | 7 | 8 | 9 | 10 | 11 |
| Content of fluorescent agent (*1) | mass % | — | — | — | — | — | — |
| Content of colorant (*1) | mass % | — | — | — | — | — | — |
| Content of yttria (*2) | mol % | 5 | 5 | 5 | 5 | 5 | 5 |
| Zirconia molded body |  |  |  |  |  |  |  |
| ΔL*(W − B) | — | 14.8 | 13.0 | 14.8 | 13.0 | 14.2 | 14.3 |
| Fraction of monoclinic crystal | % | 100 | 100 | 100 | 100 | 73 | 60 |
| Fraction of undissolved yttria | % | 7.1 | 7.2 | 7.0 | 7.1 | 3.3 | 1.3 |
| Zirconia pre-sintered body |  |  |  |  |  |  |  |
| ΔL*(W − B) | — | 13.9 | 12.2 | 13.8 | 12.4 | 13.5 | 13.4 |
| Fraction of monoclinic crystal | % | 92 | 94 | 95 | 93 | 69 | 57 |
| Fraction of undissolved yttria | % | 6.8 | 7.0 | 6.8 | 7.0 | 3.2 | 1.1 |
| Zirconia sintered body |  |  |  |  |  |  |  |
| Crystal grain size | nm | 83 | 83 | 84 | 83 | 81 | 81 |
| Three-point flexural strength | MPa | 856 | 785 | 827 | 803 | 801 | 782 |
| Light transmittance (700 nm wavelength, 0.5 mm thickness) | % | 47 | 41 | 46 | 42 | 43 | 41 |
| Linear light transmittance (1.0 mm thickness) | % | 9.8 | 7.0 | 8.8 | 7.0 | 8.3 | 7.6 |
| Fraction of cubic crystal | % | 100 | 100 | 100 | 100 | 100 | 100 |
| Fraction of monoclinic crystal after hot-water treatment | % | 0 | 0 | 0 | 0 | 0 | 0 |

(*1) Content relative to the mass of zirconia (the content is in terms of an oxide of metallic element)
(*2) Fraction of the number of moles of yttria with respect to the total number of moles of zirconia and yttria The zirconia molded body was pre-sintered at 500° C. for 2 hours under ordinary pressure to obtain a zirconia pre-sintered body. Further, the zirconia pre-sintered body was sintered at 1,100° C. for 10 minutes under ordinary pressure to obtain a zirconia sintered body containing 5 mol % yttria. The obtained zirconia sintered body was white in color. The measurement results are presented in Table 2.

Example 11

A 1.0-L mixed aqueous solution of 0.62 mol/L zirconium oxychloride and 0.066 mol/L yttrium chloride, and 0.5 L of a 1.9 mol/L aqueous solution of sodium hydroxide were separately prepared.

After pouring 1.0 L of purified water into a precipitation vessel, the mixed aqueous solution and the sodium hydroxide aqueous solution were simultaneously poured into the vessel to obtain a slurry through coprecipitation of zirconium oxychloride and yttrium chloride.

The invention claimed is:

1. A zirconia molded body, comprising:
   zirconia particles comprising 2.0 to 9.0 mol % yttria, having an average primary particle diameter of less than 60 nm, and comprising a monoclinic crystal system in a fraction of 55% or more,
   wherein the zirconia molded body comprises 1% or more undissolved yttria.

2. The zirconia molded body of claim 1, wherein the zirconia particles comprise 0.5 mass % or less zirconia particles having a particle diameter of more than 100 nm.

3. The zirconia molded body of claim 1, having ΔL*(W−B) of 5 or more through a thickness of 1.5 mm.

4. The zirconia molded body of claim 1, wherein the zirconia molded body has a three-point flexural strength of 500 MPa or more after being sintered at a temperature in a range of from 900 to 1200° C. under ordinary pressure.

5. The zirconia molded body of claim 1, wherein the zirconia molded body has a transmittance of 40% or more for light of 700 nm wavelength through a thickness of 0.5 mm after being sintered at a temperature in a range of from 900 to 1200° C. under ordinary pressure.

6. The zirconia molded body of claim 1, wherein the zirconia molded body comprises a monoclinic crystal system is in a fraction of 5% or less with respect to a tetragonal crystal system and a cubic crystal system after being sintered at a temperature in a range of from 900 to 1200° C. under ordinary pressure and then immersed in 180° C. hot water for 5 hours.

7. The zirconia molded body of claim 1, having $\Delta L^*(W-B)$ of 5 or more through a thickness of 1.5 mm after being sintered at a temperature in a range of from 200 to 800° C.

8. A zirconia pre-sintered body, comprising:
zirconia particles comprising 2.0 to 9.0 mol % yttria and comprising a monoclinic crystal system in a fraction of 55% or more; and
1% or more undissolved yttria,
wherein the zirconia pre-sintered body has $\Delta L^*(W-B)$ of 5 or more through a thickness of 1.5 mm.

9. The zirconia pre-sintered body of claim 8, having a three-point flexural strength of 500 MPa or more after being sintered at a temperature in a range of from 900 to 1200° C. under ordinary pressure.

10. The zirconia pre-sintered body of claim 8, having a transmittance of 40% or more for light of 700 nm wavelength through a thickness of 0.5 mm after being sintered at a temperature in a range of from 900 to 1200° C. under ordinary pressure.

11. The zirconia pre-sintered body of claim 8, wherein the zirconia pre-sintered body comprises a monoclinic crystal system in a fraction of 5% or less with respect to a tetragonal crystal system and a cubic crystal system after being sintered at 900 to 1200° C. under ordinary pressure and then immersed in 180° C. hot water for 5 hours.

12. A method for producing a zirconia pre-sintered body, the method comprising:
pre-sintering the zirconia molded body of claim 1 at a temperature in a range of from 200 to 800° C.

13. A zirconia sintered body, comprising:
a fluorescent agent; and
2.0 to 9.0 mol % yttria,
wherein the zirconia sintered body has a crystal grain size of 180 nm or less, and
wherein the zirconia sintered body has a linear light transmittance of 1% or more through a thickness of 1.0 mm.

14. The zirconia sintered body of claim 13, having a three-point flexural strength of 500 MPa or more.

15. The zirconia sintered body of claim 13, having a transmittance of 40% or more for light of 700 nm wavelength through a thickness of 0.5 mm.

16. The zirconia sintered body of claim 13, comprising a monoclinic crystal system in a fraction of 5% or less with respect to a tetragonal crystal system and a cubic crystal system after being immersed in 180° C. hot water for 5 hours.

17. A method for producing a zirconia sintered body, the method comprising:
sintering the zirconia molded body of claim 1 at a temperature in a range of from 900 to 1200° C. under ordinary pressure.

18. A method for producing a zirconia sintered body, the method comprising:
sintering the zirconia pre-sintered body of claim 8 at a temperature in a range of from 900 to 1200° C. under ordinary pressure.

* * * * *